United States Patent
Chand et al.

(10) Patent No.: US 9,403,769 B2
(45) Date of Patent: Aug. 2, 2016

(54) SMALL MOLECULE INHIBITORS OF PFKFB3 AND GLYCOLYTIC FLUX AND THEIR METHODS OF USE AS ANTI-CANCER THERAPEUTICS

(75) Inventors: Pooran Chand, Birmingham, AL (US); Jason A. Chesney, Louisville, KY (US); Brian F. Clem, Louisville, KY (US); Gilles H. Tapolsky, Louisville, KY (US); Sucheta Telang, Louisville, KY (US); John O. Trent, Louisville, KY (US)

(73) Assignees: Advanced Cancer Therapeutics, LLC, Louisville, KY (US); University of Louisville Research Foundation, Inc., Louisville, KY (US)

( * ) Notice: Subject to any disclaimer, the term of this patent is extended or adjusted under 35 U.S.C. 154(b) by 603 days.

(21) Appl. No.: 13/580,558

(22) PCT Filed: Feb. 22, 2011

(86) PCT No.: PCT/US2011/025691
§ 371 (c)(1),
(2), (4) Date: Aug. 22, 2012

(87) PCT Pub. No.: WO2011/103557
PCT Pub. Date: Aug. 25, 2011

(65) Prior Publication Data
US 2013/0059879 A1    Mar. 7, 2013

Related U.S. Application Data

(60) Provisional application No. 61/306,759, filed on Feb. 22, 2010.

(51) Int. Cl.
*C07D 209/60* (2006.01)
*C07D 401/06* (2006.01)
*C07D 471/04* (2006.01)

(52) U.S. Cl.
CPC ............ *C07D 209/60* (2013.01); *C07D 401/06* (2013.01); *C07D 471/04* (2013.01)

(58) Field of Classification Search
None
See application file for complete search history.

(56) References Cited

U.S. PATENT DOCUMENTS

2003/0139404 A1*   7/2003   Haag et al.
2009/0074884 A1    3/2009   Chesney et al.

OTHER PUBLICATIONS

Parrish et al., Bioorganic & Medicinal Chemistry, 2003, vol. 11, pp. 3815-3838.*
International Search Report in PCT/US2011/25691, May 31, 2011.
Kim et al, Crytal Structure of the Hypoxi-inducible Form of 6-Phosphofructo-2-kinase/fructose-2,6-biphosphatase (PFKFB3), Journal of Biological Chemistry, vol. 281(5), Feb. 3, 2006.

\* cited by examiner

*Primary Examiner* — Savitha Rao
*Assistant Examiner* — Gregg Polansky
(74) *Attorney, Agent, or Firm* — Dinsmore & Shohl LLP

(57) ABSTRACT

Small molecule inhibitors of 6-phosphofructo-2-kinase/fructose-2,6-biphosphatase 3 (PFKFB3) having the following formula: Formula (1) are provided herein. Also provided herein are pharmaceutical compositions containing Formula I compounds, together with methods of treating cancer, methods of inhibiting PFK.FB3 enzymatic activity, methods of inhibiting glycolytic flux, and methods of treating tumors by administering an effective amount of a Formula I compound.

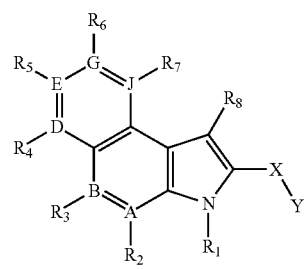

Formula (I)

12 Claims, 6 Drawing Sheets

US 9,403,769 B2

SMALL MOLECULE INHIBITORS OF PFKFB3 AND GLYCOLYTIC FLUX AND THEIR METHODS OF USE AS ANTI-CANCER THERAPEUTICS

This application claims priority under 35 U.S.C. §119(e) to U.S. Provisional Application Ser. No. 61/306,759, filed Feb. 22, 2010, which application is hereby incorporated by reference in its entirety.

The presently-disclosed subject matter relates to small-molecule inhibitors of 6-phosphofructo-2-kinase/fructose-2,6-biphosphatase 3 (PFKFB3) and methods of using the same. In particular, the presently-disclosed subject matter relates to substituted benzindoles as PFKFB3 inhibitors and methods of using these inhibitors to reduce cellular glycolytic flux and/or treat cancer and tumors in mammals.

The glycolytic pathway is a ten-step series of reactions that forms the major metabolic pathway in nearly all organisms. Flux through the glycolytic pathway is adjusted in response to conditions both inside and outside the cell. Irreversible glycolytic reactions are those catalyzed by hexokinase, phosphofructokinase, and pyruvate kinase. In metabolic pathways, such enzymes are potential targets for control, and all three enzymes serve this purpose in glycolysis. The PFKFB enzymes (PFKFB 1-4) synthesize fructose-2,6-bisphosphate (F2,6BP) which activates 6-phosphofructo-1-kinase (PFK-1), an essential control point in the glycolytic pathway.

Neoplastic cells preferentially utilize glycolysis to satisfy their increased needs for energy and biosynthetic precursors. Malignant tumor cells have glycolytic rates that are up to 200 times higher than those of their normal tissues of origin. One cancer attack strategy has been to treat cancer by starving cancerous cells in various ways. Despite greater understanding and pharmaceutical advances in the diagnosis and treatment of cancer, it is still estimated that nearly 13% of all human deaths last year were due to cancer. Thus, there remains a need for additional anti-cancer therapeutics, particularly those which target neoplastic cells via mechanisms over-expressed in cancer cells, such as glycolytic flux, which is increased in cancer cells.

6-phosphofructo-2-kinase/fructose-2,6-biphosphatase 3, or PFKFB3, is a valuable molecular target for the development of anti-cancer therapeutics. Accordingly, provided herein are novel small molecule inhibitors of PFKFB3 having the following formula:

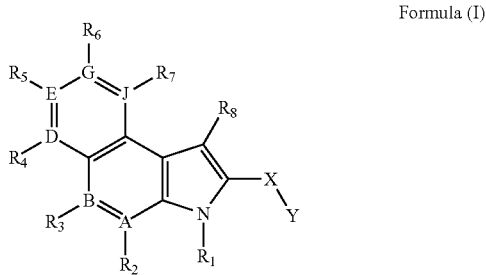

Formula (I)

In another embodiment, a pharmaceutical composition for the treatment of cancer is provided, the composition comprising a Formula I compound and at least one pharmaceutically acceptable carrier.

In another embodiment, a method of treating cancer is provided, the method comprising administering to a subject in need thereof an effective amount of a Formula I compound.

In another embodiment, a method of treating a tumor is provided, the method comprising administering to a subject in need thereof an effective amount of a Formula I compound.

In still another embodiment, a method of inhibiting glycolytic flux in a cell is provided, the method comprising contacting the cell with an effective amount of a Formula I compound.

In another embodiment, a method of inhibiting enzymatic activity of PFKFB3 in a cell is provided, the method comprising contacting the cell with an effective amount of a Formula I compound.

These and other objects, features, embodiments, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified.

FIG. 1 shows the time vs. plasma concentration pharmacokinetic profile of ACT-PFK-065 in BalbC mice (IV dosing, 10 mg/kg; IP dosing, 10 mg/kg; PO dosing, 20 mg/kg).

FIG. 2 shows the time vs. plasma concentration pharmacokinetic profile of ACT-PFK-095 in male Sprague-Dawley rats (IV dosing, 5 mg/kg; IP dosing, 10 mg/kg; PO dosing, 10 mg/kg).

Figure 1:
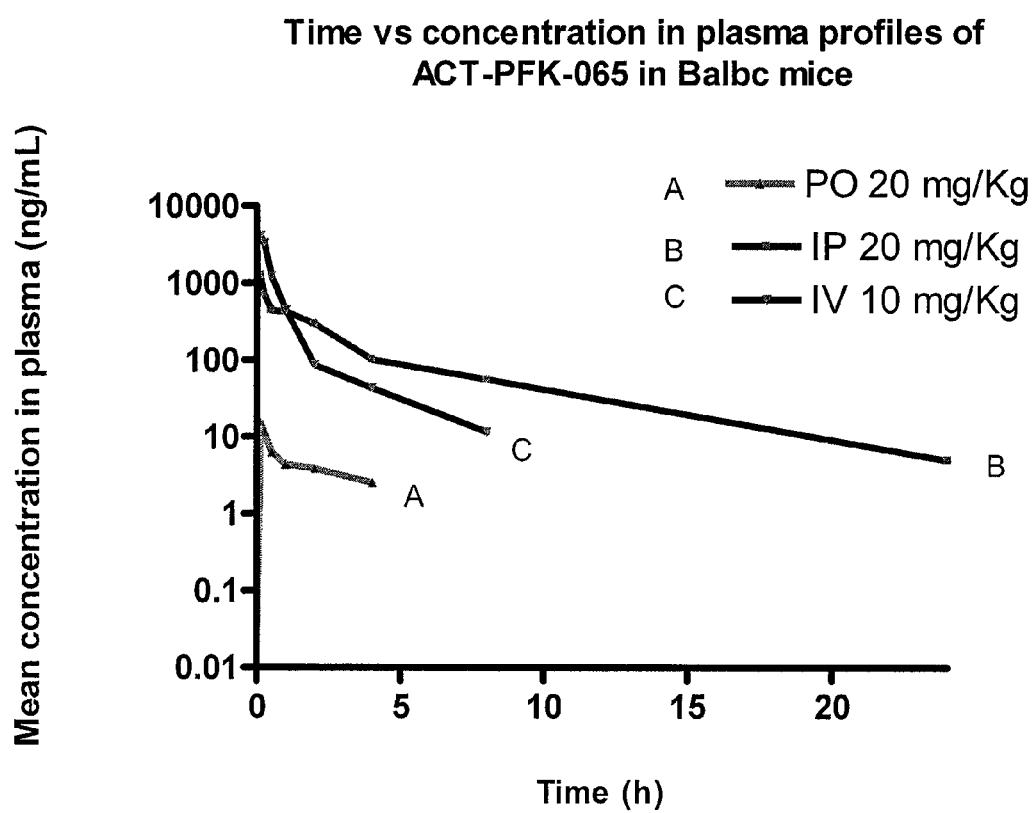

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood by one of ordinary skill in the art, definitions are set forth to facilitate explanation of the presently-disclosed subject matter.

Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

Throughout the specification and claims, a given chemical formula or name shall encompass all tautomers and optical and stereoisomers, as well as racemic mixtures where such isomers and mixtures exist.

The term "cancer" as used herein refers to diseases caused by uncontrolled cell division and the ability of cells to metastasize, or to establish new growth in additional sites. The terms "malignant," "malignancy," "neoplasm," "tumor" and variations thereof refer to cancerous cells or groups of cancerous cells.

The term "anti-cancer agent," "anti-cancer compound," "anti-neoplastic compound," "anti-tumor agent," "anti-cancer therapeutic" and variations thereof as used herein refer to compounds that can prevent the proliferation of cancer cells and tumors or kill cancer cells.

Specific types of cancer include, but are not limited to, skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood, and lymphoid cancers.

The term "competitive inhibitor" refers to an inhibitor whose binding to an enzyme prevents the binding of the enzyme's normal substrate.

As used herein, the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to ($C_1$-$C_6$) linear or branched alkyls. In other specific embodiments, "alky" comprises ($C_1$-$C_3$) linear or branched alkyl.

Alkyl groups can optionally be substituted (a "substituted alkyl") with one or more alkyl group substituents, which can be the same or different. The term "alkyl group substituent" includes but is not limited to alkyl, substituted alkyl, halogen, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl. In certain embodiments, "cycloalkyl" comprises ($C_3$-$C_8$) cycloalkyl.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings. In specific embodiments, aryl comprises ($C_6$-$C_{14}$) aryl ring structures.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroaryl" is used herein to refer to aromatic ring structures comprising at least one heteroatom as a ring member. Heteroaryl rings are monocyclic or fused polycyclic ring systems. Monocyclic heteroaryl rings contain from 5 to 9 member atoms (carbon and heteroatoms), more specifically 5 or 6 member atoms in the ring. Polycyclic heteroaryl rings contain from 8 to 13 member atoms, more specifically 8 to 12 member atoms in the ring. Polycyclic heteroaryl rings include ring systems wherein at least one ring is heteroaryl (the second ring may be aryl, heteroaryl, or cycloalkyl). In specific embodiments, bicyclic heteroaryl ring systems comprise 5-, 6-, or 7-membered rings fused to 5-, 6-, or 7-membered rings. In other specific embodiments, heteroaryl comprises from 5 to 13 member atoms.

Heteroaryl rings may be substituted with at least one substituent on the ring. In certain embodiments, heteroaryl rings may be substituted with halogen, cyano, nitro, hydroxy, amino, alkyl, lower alkenyl, lower alkynyl, heteroalkyl, aryloxy, alkoxy, methylenedioxy, thioalkoxy, thioaryloxy, or any combination thereof.

Specific examples of aryl groups, including heteroaryl groups, include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, oxazole benzimidazole, azaindole, and the like.

"Heteroatom" refers to a non-carbon atom as a ring member in a heteroaryl ring structure. In certain embodiments, the heteroatom can be nitrogen, oxygen, or sulfur. Heteroatoms can contain further substituents, such that in certain embodiments, heteroaryl rings can comprise ring members selected from the group consisting of N, N=O, NH, N—($C_1$-$C_6$)-alkyl, O, or S. In certain embodiments, a heteroaryl can contain from 1 to 4 heteroatoms in the heteroaryl ring. In other embodiments, a heteroaryl can contain 1, 2, 3, or 4 heteroatoms in the heteroaryl ring. In a very specific embodiment, a heteroaryl can contain 1 heteroatom in the heteroaryl ring.

In specific embodiments, heteroaryl ring structures are aza ring structures. As used herein, the term "aza" refers to a heterocyclic ring structure containing at least one nitrogen atom. Specific examples of aza groups include, but are not limited to, pyrrolidine, piperidine, quinuclidine, pyridine, pyrrole, indole, purine, pyridazine, pyrimidine, and pyrazine.

The term "azaaryl" refers to a heterocyclic aryl group wherein one or more of the atoms of the aryl group ring or rings is nitrogen. Examples of azaaryl groups include monocyclic or bicyclic mono- or diazaaryl (i.e., an aryl group comprising two nitrogen atoms), which is unsubstituted or substituted by a member selected from the group consisting of lower alkyl, for example methyl, lower alkoxy, for example methoxy, and/or halogen, for example chlorine or bromine. Therefore, the term "azaaryl" refers to groups including, but not limited to, pyridine, pyridazine, pyrimidine, pyrazine, quinoline, quinaldine, quinoxaline, and substituted analogs thereof. In some embodiments, the azaaryl group is pyridyl, for example 2-, 3- or 4-pyridyl; quinolinyl or isoquinolinyl, for example 4-quinolinyl or 1-isoquinolinyl; imidazolyl; pyrimidinyl, for example 2- or 4-pyrimidinyl; pyridazinyl, for example 3-pyridazinyl; or pyrazinyl, for example 2-pyrazinyl.

"Alkoxy" or "alkoxyl" refer to an alkyl-O— group wherein alkyl is as previously described. The term "alkoxy" as used herein can refer to, for example, methoxy, ethoxy, propoxy, isopropoxy, butoxy, t-butoxy, and pentoxl. The term "oxyalkyl" can be used interchangeably with "alkoxy." In certain embodiments, alkoxy comprises ($C_1$-$C_6$) alkoxy.

In other specific embodiments, alkoxy comprises ($C_1$-$C_3$) alkoxy.

The term "carboxyl" refers to the —COOH group.

The term "hydroxyl" refers to the —OH group.

The terms "halo," "halide," or "halogen" as used herein refer to fluoro, chloro, bromo, and iodo groups.

As used herein, the term "acyl" refers to an organic carboxylic acid group wherein the —OH of the carboxyl group has been replaced with another substituent (i.e., as represented by RCO—, wherein R is an alkyl, aralkyl or aryl group as defined herein, including substituted alkyl, aralkyl, and aryl groups). As such, the term "acyl" specifically includes arylacyl groups, such as an acetylfuran and a phenacyl group. Specific examples of acyl groups include acetyl and benzoyl.

"Aryloxyl" refers to an aryl-O— group wherein the aryl group is as previously described, including a substituted aryl.

The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NR-group wherein acyl is as previously described and R is H or alkyl. Thus, the "acylamino" group can have the structure —NR—C(=O)—R', wherein R' is alkyl, aryl, aralkyl, and the like.

The term "amino" refers to the —$NH_2$ group.

The term "carbonyl" refers to the —(C=O)— group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

When the term "independently selected" is used, the substituents being referred to (e.g., R groups, such as groups $R_2$-$R_7$, or groups A, B, D, E, G, or J), can be identical or different. For example, both $R_2$ and $R_3$ can be the same substituent, or $R_2$ and $R_3$ can each be different substituents selected from a specified group.

I. Compounds

In one embodiment, the PFKFB3 inhibitors of the present invention have the following structural formula:

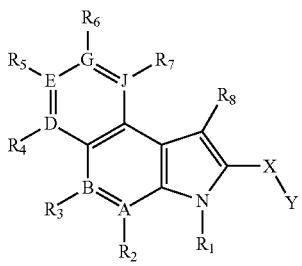

Formula (I)

wherein:

A, B, D, E, G and J are independently selected from the group consisting of N or C substituted with one of $R_2$, $R_3$, $R_4$, $R_5$, $R_6$ or $R_7$, wherein if A, B, D, E, G, or J are N, then $R_2$, $R_3$, $R_4$, $R_5$, $R_6$ or $R_7$ represent a free electron pair at the N atom;

$R_1$ is selected from the group consisting of hydrogen and linear or branched $(C_1-C_6)$-alkyl;

$R_2$, $R_3$, $R_4$, $R_5$, $R_6$ and $R_7$ are independently of one another, when attached to N, a free electron pair, or, when attached to C, are selected from the group consisting of hydrogen, halogen, —COOH, linear or branched $(C_1-C_6)$-alkyl, linear or branched $(C_1-C_6)$-alkoxy, hydroxyl, —NH$_2$, N—$(C_1-C_6)$-alkyl, N-di-$(C_1-C_6)$-alkyl, and —SO$_2$CH$_3$;

$R_8$ is selected from the group consisting of hydrogen and linear or branched $(C_1-C_6)$-alkyl;

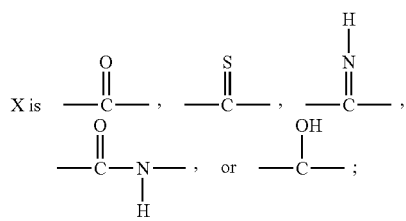

and

Y is selected from the group consisting of substituted or unsubstituted $(C_6-C_{14})$-aryl, substituted or unsubstituted heteroaryl comprising from 5 to 13 member atoms and having at least one of N, N=O, NH, N—$(C_1-C_6)$-alkyl, O or S as ring members, and substituted or unsubstituted $(C_3-C_8)$-cycloalkyl.

In another embodiment of the invention, PFKFB3 inhibitor compounds have the following structural formula, wherein A, B, D, E, G, J, X, Y, and $R_1$-$R_8$ are defined as above for Formula I:

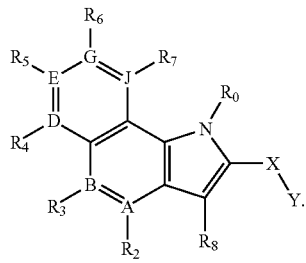

Formula (II)

In another embodiment of the invention, PFKFB3 inhibitor compounds have the following structural formula, wherein A, B, D, E, G, J, X, Y, and $R_1$-$R_8$ are defined as above for Formula I:

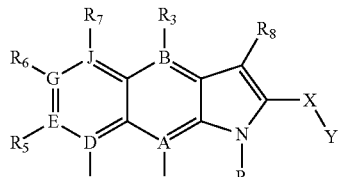

Formula (III)

Examples of Formula I and Formula II compounds are shown in Table 1, below.

TABLE 1

Exemplary Compounds

| Compound Number | Mw | Structure, Name and NMR Data |
|---|---|---|
| ACT-PFK-061 | 271.1 | ![structure] (1H-Benzo[g]indol-2-yl)-phenyl-methanone. The compound may be prepared using Scheme 5. $^1$H NMR (300 MHz, DMSO-d$_6$): δ 12.92 (s, 1 H), 8.87-8.85 (m, 1 H), 7.97-7.95 (m, 3 H), 7.74-7.52 (m, 7 H), 7.26 (m, 1 H). |

TABLE 1-continued

Exemplary Compounds

| Compound Number | Mw | Structure, Name and NMR Data |
|---|---|---|
| ACT-PFK-065 | 271.1 | 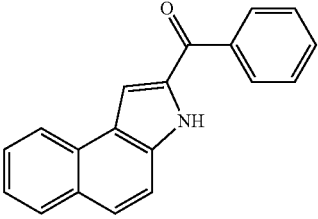 [SMILES: O=C(c1ccccc1)c1cc2c(ccc3ccccc32)[nH]1] (3H-Benzo[e]indol-2-yl)-phenyl-methanone. The compound may be prepared using Scheme 2. $^1$H NMR (300 MHz, DMSO-d$_6$) δ 12.43 (s, 1 H), 8.39 (d, J = 6.0. Hz, 1 H), 8.01-7.93 (m, 3H), 7.80-7.72 (m, 2 H), 7.69-7.65 (m. 1H), 7.63-7.45 (m, 4 H), 7.48-7.43 (m, 1H). |
| ACT-PFK-093 | 301.3 | 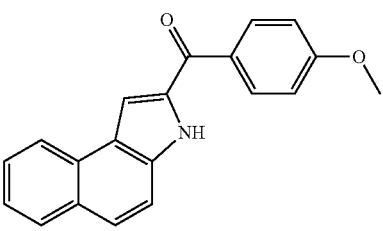 [SMILES: COc1ccc(C(=O)c2cc3c(ccc4ccccc43)[nH]2)cc1] (3H-Benzo[e]indol-2-yl)-(4-methoxy-phenyl)-methanone. The compound may be prepared using Scheme 1. $^1$H NMR (300 MHz, DMSO-d$_6$) δ 12.36 (s, 1 H), 8.39 (d, J = 8.1. Hz, 1 H), 8.03 (d, J = 8.7 Hz, 2H), 7.94 (d, J = 6.0 Hz, 1 H), 7.81-7.75 (m. 2H), 7.64-7.56 (m, 2 H), 7.45 (s, 1 H), 7.16 (d, J = 8.4. Hz, 2H), 3.90 (s, 3H). |
| ACT-PFK-095 | 272.3 | 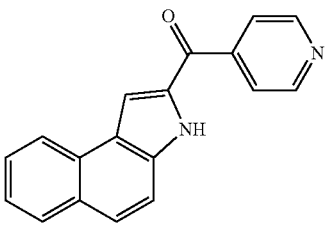 [SMILES: O=C(c1ccncc1)c1cc2c(ccc3ccccc32)[nH]1] (3H-Benzo[e]indol-2-yl)-pyridin-4-yl-methanone. The compound may be prepared using Scheme 3. $^1$H NMR (300 MHz, DMSO-d$_6$): δ 12.50 (s, 1 H), 8.87-8.85 (m, 2 H), 8.42-8.39 (m, 1 H), 7.97-7.94 (m, 1 H), 7.88-7.86 (m, 3 H), 7.83-7.80 (m, 1 H), 7.65-7.58 (m, 2 H), 7.50-7.44 (m, 1 H) |
| ACT-PFK-095•HCl | 308.76 | 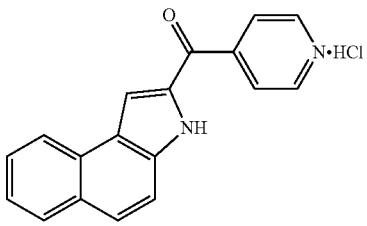 HCl salt of (3H-Benzo[e]indol-2-yl)-pyridin-4-yl-methanone. The compound may be prepared using Scheme 3. $^1$H NMR (300 MHz, DMSO-d$_6$) δ 12.66 (s, 1 H), 9.02-9.00 (m, 2 H), 8.36 (d, J = 8.1 Hz, 1 H), 8.15-8.14 (m, 2 H), 7.96 (d, J = 7.8 Hz, 1 H), 7.89-7.82 (m, 2 H), 7.65-7.57 (m, 2 H), 7.50-7.45 (m, 1 H). |

TABLE 1-continued

Exemplary Compounds

| Compound Number | Mw | Structure, Name and NMR Data |
|---|---|---|
| ACT-PFK-096 | 301.34 | 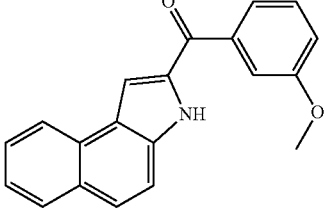<br>(3H-Benzo[e]indol-2-yl)-(3-methoxy-phenyl)-methanone. The compound may be prepared using Scheme 1. $^1$H NMR (300 MHz, DMSO-d$_6$) δ 12.43 (s, 1 H), 8.40 (d, J = 9.0 Hz, 1 H), 7.94 (d, J = 9.0 Hz, 1 H), 7.82-7.76 (m, 2 H), 7.64-7.43 (m, 6 H), 7.27 (d, J = 6.0 Hz, 1 H), 3.88 (s, 3 H). |
| ACT-PFK-097 | 272.3 | 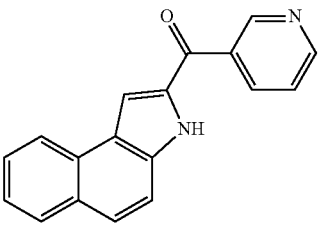 [SMILES: O=C(c1cccnc1)c1cc2c(ccc3ccccc32)[nH]1]<br>(3H-Benzo[e]indol-2-yl)-pyridin-3-yl-methanone. The compound may be prepared using Scheme 1. $^1$H NMR (300 MHz, DMSO-d$_6$) δ 12.54 (s, 1 H), 9.14 (d, J = 1.5 Hz, 1 H), 8.89-8.87 (dd, J = 4.8, 1.2 Hz, 1 H), 8.44-8.35 (m, 2 H), 7.96-7.90 (m, 2 H), 7.82-7.79 (m, 1 H), 7.69-7.56 (m, 3 H), 7.47 (t, J = 7.2 Hz 1 H). |
| ACT-PFK-098 | 301.34 | 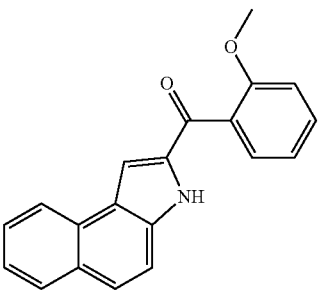 [SMILES: COc1ccccc1C(=O)c1cc2c(ccc3ccccc32)[nH]1]<br>(3H-Benzo[e]indol-2-yl)-(2-methoxy-phenyl)-methanone. The compound may be prepared using Scheme 1. $^1$H NMR (300 MHz, DMSO-d$_6$) δ 12.36 (s, 1 H), 8.27 (d, J = 7.8 Hz, 1 H), 7.92 (d, J = 7.8 Hz, 1 H), 7.77-7.74 (m, 1 H), 7.62-7.41 (m, 6 H), 7.23 (d, J = 8.4 Hz, 1 H), 7.11 (t, J = 7.2 Hz, 1 H), 3.77 (s, 3 H). |
| ACT-PFK-099 | 287.31 | 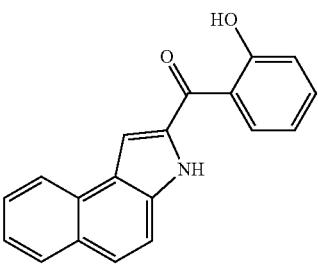 [SMILES: O=C(c1cc2c(ccc3ccccc32)[nH]1)c1ccccc1O]<br>(3H-Benzo[e]indol-2-yl)-(2-hydroxy-phenyl)-methanone. The compound may be prepared using Scheme 1. $^1$H NMR (300 MHz, DMSO-d$_6$) δ 11.01 (s, 1 H), 8.10 (d, J = 9.0 Hz, 1 H), 8.01-7.99 (m, 2 H), 7.63-7.46 (m, 6 H), 7.02 (d, J = 9.0 Hz, 1 H), 6.91-6.86 (m, 1 H). |

TABLE 1-continued

Exemplary Compounds

| Compound Number | Mw | Structure, Name and NMR Data |
|---|---|---|
| ACT-PFK-100 | 287.3 | 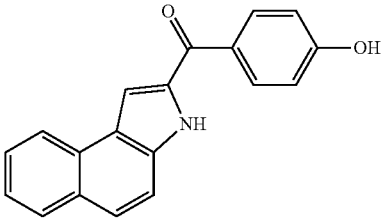 [SMILES: O=C(c1ccc(O)cc1)c1cc2c(ccc3ccccc32)[nH]1]<br>(3H-Benzo[e]indol-2-yl)-(4-hydroxy-phenyl)-methanone. The compound may be prepared using Scheme 1. $^1$H NMR (300 MHz, DMSO-d$_6$) δ 12.32 (s, 1 H), 10.36 (s, 1 H), 8.40 (d, J = 9.0 Hz, 1 H), 7.97-7.93 (m, 3 H), 7.81-7.74 (m, 2H), 7.64-7.55 (m, 2 H), 7.47-7.45 (m, 1 H), 6.99-6.96 (m, 2 H) |
| ACT-PFK-101 | 285.34 | 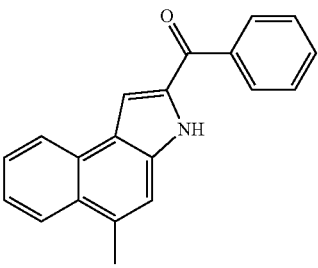 [SMILES: Cc1cc2[nH]c(C(=O)c3ccccc3)cc2c2ccccc12]<br>(5-Methyl-3H-benzo[e]indol-2-yl)-phenyl-methanone. The compound may be prepared using Scheme 1. $^1$H NMR (300 MHz, DMSO-d$_6$) δ 12.32 (s, 1 H), 8.40 (d, J = 7.2 Hz, 1 H), 8.04-7.97 (m, 3 H), 7.76-7.68 (m, 2 H), 7.64-7.53 (m, 5 H), 2.70 (s, 3 H). |
| ACT-PFK-102 | 272.30 | 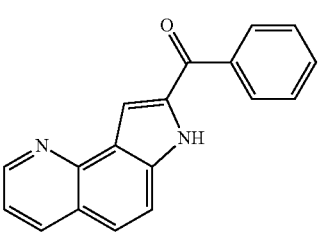 [SMILES: O=C(c1ccccc1)c1cc2c(ccc3cccnc32)[nH]1]<br>Phenyl-(7H-pyrrolo[2,3-h]quinolin-8-yl)-methanone. The compound may be prepared using Scheme 1. $^1$H NMR (300 MHz, DMSO-d$_6$) δ 12.66 (s, 1 H), 8.87-8.86 (m, 1 H), 8.42-8.38 (dd, J = 8.1, 1.5 Hz, 1 H), 8.00 (d, J = 6.9 Hz, 2 H), 7.84-7.82 (m, 1 H), 7.75-7.64 (m, 5 H), 7.53-7.49 (m, 1 H). |
| ACT-PFK-103 | 287.3 | 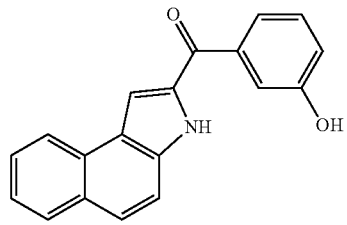 [SMILES: O=C(c1cccc(O)c1)c1cc2c(ccc3ccccc32)[nH]1]<br>(3H-Benzo[e]indol-2-yl)-(3-hydroxy-phenyl)-methanone. The compound may be prepared using Scheme 1. $^1$H NMR (300 MHz, DMSO-d$_6$) δ 12.40 (s, 1 H), 9.88 (s, 1H), 8.38 (d, J = 8.1 Hz, 1 H), 7.94 (d, J = 8.1 Hz, 1 H), 7.78-7.76 (m, 2H), 7.64-7.54 (m. 2H), 7.48-7.35 (m, 4H), 7.10-7.07 (m, 1H). |

TABLE 1-continued

Exemplary Compounds

| Compound Number | Mw | Structure, Name and NMR Data |
|---|---|---|
| ACT-PFK-104 | 289.30 | 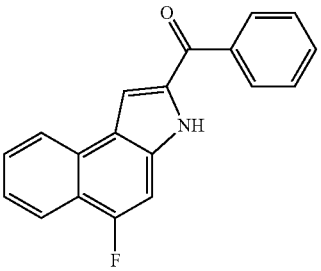 [SMILES: O=C(c1ccccc1)c1cc2c(cc(F)c3ccccc32)[nH]1]<br>(5-Fluoro-3H-benzo[e]indol-2-yl)-phenyl-methanone. The compound may be prepared using Scheme 1. $^1$H NMR (300 MHz, DMSO-d$_6$) δ 12.48 (s, 1 H), 8.47 (d, J = 8.4 Hz, 1 H), 8.06 (d, J = 8.1 Hz, 1 H), 7.99-7.96 (m, 2 H), 7.84 (d, J = 1.8 Hz, 1 H), 7.70-7.55 (m, 5 H), 7.38 (d, J = 11.1 Hz, 1 H). |
| ACT-PFK-105 | 306.7 | 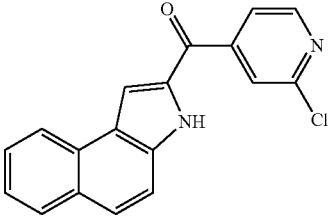 [SMILES: O=C(c1ccnc(Cl)c1)c1cc2c(ccc3ccccc32)[nH]1]<br>(3H-benzo[e]indol-2-yl)-(2-chloro-pyridin-4-yl)-methanone. The compound may be prepared using Scheme 1. $^1$H NMR (300 MHz, DMSO-d$_6$) δ 12.75 (s, 1 H), 8.91 (d, J = 8.4 Hz, 1 H), 8.84 (d, J = 5.4 Hz, 2 H), 8.02 (d, J = 7.8 Hz, 1 H) 7.88-7.86 (m, 1 H), 7.72 (d, J = 5.7 Hz, 2 H), 7.69-7.61 (m, 2 H), 7.57-7.55 (m, 1 H). |
| ACT-PFK-106 | 288.3 | 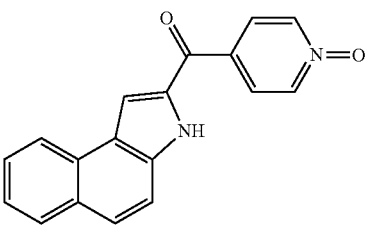 [SMILES: O=C(c1cc[n+]([O-])cc1)c1cc2c(ccc3ccccc32)[nH]1]<br>(3H-benzo[e]indol-2-yl)-(1-oxy-pyridin-4-yl)-methanone. The compound may be prepared using Scheme 1. $^1$H NMR (300 MHz, DMSO-d$_6$) δ 12.51 (s, 1 H), 8.40 (d, J = 9.0 Hz, 3 H), 8.01-7.94 (m, 4 H), 7.80 (d, J = 9.0 Hz, 1 H), 7.64-7.58 (m, 2 H), 7.48 (d, J = 9.0 Hz, 1 H). |
| ACT-PFK-107 | 275.34 | 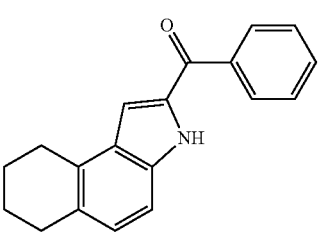 [SMILES: O=C(c1ccccc1)c1cc2c3c(ccc2[nH]1)CCCC3]<br>Phenyl-(6,7,8,9-tetrahydro-3H-benzo[e]indol-2-yl)-methanone. The compound may be prepared using Scheme 1. $^1$H NMR (300 MHz, DMSO-d$_6$) δ 11.86 (s, 1 H), 7.93 (d, J = 7.2 Hz, 2 H), 7.71-7.57 (m, 3 H), 7.25-7.22 (m, 1 H), 7.03-7.00 (m, 2 H), 2.89 (brs, 2 H), 2.76 (brs, 2 H), 1.80 (brs, 4 H). |

TABLE 1-continued

Exemplary Compounds

| Compound Number | Mw | Structure, Name and NMR Data |
|---|---|---|
| ACT-PFK-108 | 317.34 | 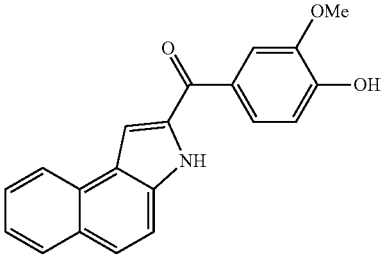 [SMILES: COc1cc(C(=O)c2cc3c(ccc4ccccc43)[nH]2)ccc1O]<br>(3H-Benzo[e]indol-2-yl)-(4-hydroxy-3-methoxylthenyl)-methanone. The compound may be prepared using Scheme 1. $^1$H NMR (300 MHz, DMSO-d$_6$) δ 12.30 (s, 1 H), 9.98 (s, 1 H), 8.41 (d, J = 9.0 Hz, 1 H), 7.95-7.73 (m, 3 H,), 7.64-7.42 (m, 5 H), 6.99 (d, J = 6.0 Hz, 1 H), 3.90 (s, 3 H). |
| ACT-PFK-109 | 407.46 | 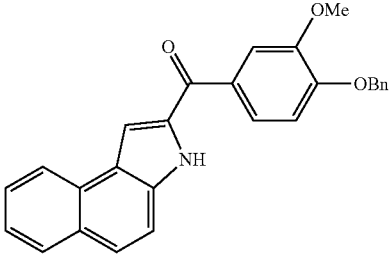 [SMILES: COc1cc(C(=O)c2cc3c(ccc4ccccc43)[nH]2)ccc1OCc1ccccc1]<br>(3H-Benzo[e]indol-2-yl)-(4-benzyloxy-3-methoxy-phenyl)-methanone. The compound may be prepared using Scheme 1. $^1$H NMR (300 MHz, DMSO-d$_6$) δ 12.35 (s, 1H), 8.42-8.40 (m, 1 H), 7.95-7.25 (m, 14 H), 5.25 (s, 2 H), 3.90 (s, 3 H). |
| ACT-PFK-110 | 329.35 | 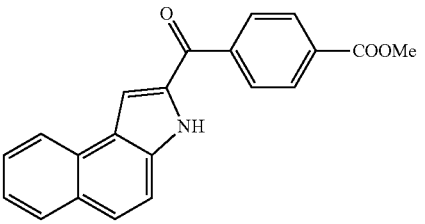 [SMILES: COC(=O)c1ccc(C(=O)c2cc3c(ccc4ccccc43)[nH]2)cc1]<br>4-(3H-Benzo[e]indole-2-carbonyl)-benzoic acid methyl ester. The compound may be prepared using Scheme 1. $^1$H NMR (300 MHz, DMSO-d$_6$) δ 12.53 (s, 1 H), 8.39 (d, J = 8.0 Hz, 1 H), 8.20-8.09 (m, 4 H), 7.95 (d, J = 8.0 Hz, 1 H), 7.84 (t, J = 9.0 Hz, 2 H), 7.65-7.56 (m, 2 H), 7.46 (t, J = 6.0 Hz, 1 H), 3.94 (s, 3 H). |
| ACT-PFK-111 | 315.32 | 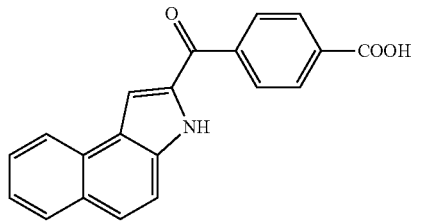 [SMILES: O=C(O)c1ccc(C(=O)c2cc3c(ccc4ccccc43)[nH]2)cc1]<br>4-(3H-Benzo[e]indole-2-carbonyl)-benzoic acid. The compound may be prepared using Scheme 1. $^1$H NMR (300 MHz, DMSO-d$_6$) δ 13.36 (s, 1 H), 12.52 (s, 1 H), 8.40 (d, J = 8.0 Hz, 1 H), 8.18-8.07 (m, 4 H), 7.95 (d, J = 8.0 Hz, 1 H), 7.82 (t, J = 9.0 Hz, 2 H), 7.65-7.55 (m, 2 H), 7.46 (t, J = 6.0 Hz, 1 H). |

TABLE 1-continued

Exemplary Compounds

| Compound Number | Mw | Structure, Name and NMR Data |
|---|---|---|
| ACT-PFK-112 | 286.33 | 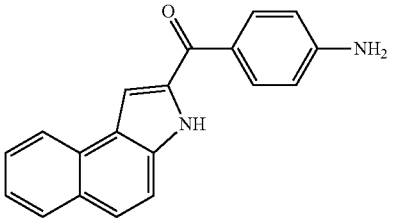 [SMILES: Nc1ccc(C(=O)c2cc3c(ccc4ccccc43)[nH]2)cc1]<br>(4-Amino-phenyl)-(3H-benzo[e]indol-2-yl)-methanone. The compound may be prepared using Scheme 4. ¹H NMR (300 MHz, DMSO-d₆) δ 12.18 (s, 1 H), 8.38 (d, J = 9.0 Hz, 1 H), 7.92 (d, J = 9.0 Hz, 1 H), 7.86-7.83 (m, 2 H), 7.76-7.70 (m, 2 H), 7.59-7.56 (m, 2 H), 7.43-7.42 (m, 1 H), 6.69 (d, J = 8.7 Hz, 2 H), 6.09 (s, 2 H). |
| ACT-PFK-113 | 435.5 | 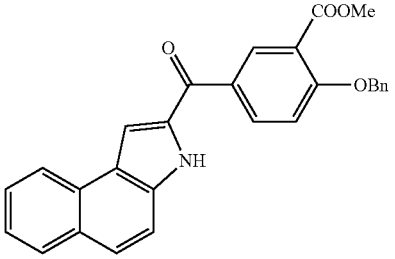 [SMILES: COC(=O)c1cc(C(=O)c2cc3c(ccc4ccccc43)[nH]2)ccc1OCc1ccccc1]<br>5-(3H-Benzo[e]indole-2-carbonyl)-2-benzyloxy-benzoic acid methyl ester. The compound may be prepared using Scheme similar to Scheme 1. ¹H NMR (300 MHz, DMSO-d₆) δ 12.44 (s, 1 H), 8.40-8.24 (m, 3 H), 7.95 (d, J = 8.1 Hz, 1 H), 7.84-7.77 (m, 2H), 7.65-7.55 (m, 4H), 7.48-7.36 (m, 5H), 5.39 (s, 2H), 3.87 (s, 3H). |
| ACT-PFK-114 | 421.4 | 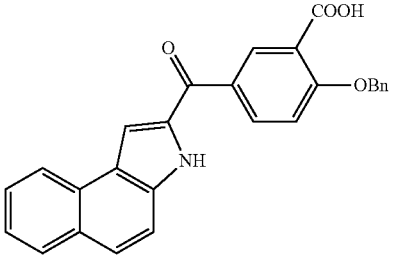 [SMILES: O=C(c1ccc(OCc2ccccc2)c(C(=O)O)c1)c1cc2c(ccc3ccccc32)[nH]1]<br>5-(3H-Benzo[e]indole-2-carbonyl)-2-benzyloxy-benzoic acidmethanone. The compound may be prepared using Scheme 1. ¹H NMR (300 MHz, DMSO-d₆) δ 12.98 (br s, 1 H), 12.42 (s, 1H), 8.20-8.45 (m, 3H), 7.96-7.76 (m, 3 H), 7.64-7.38 (m, 9H), 5.38 (s, 2H). |
| ACT-PFK-115 | 302.3 | 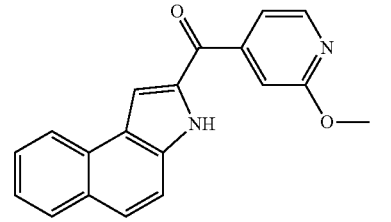 [SMILES: COc1cc(C(=O)c2cc3c(ccc4ccccc43)[nH]2)ccn1]<br>(3H-Benzo[e]indol-2-yl)-(2-methoxy-pyridin-4-yl)-methanone. The compound may be prepared using Scheme 1. ¹H NMR (300 MHz, DMSO-d₆) δ 12.53 (s, 1 H), 8.43-8.40 (m, 2H), 7.94 (d, J = 7.8 Hz, 1H). 7.86-7.79 (m, 2 H), 7.63-7.57 (m. 2H), 7.46-7.41 (m, 2 H), 7.23 (br s, 1H), 3.97 (s, 3H). |

TABLE 1-continued

Exemplary Compounds

| Compound Number | Mw | Structure, Name and NMR Data |
|---|---|---|
| ACT-PFK-116 | 319.33 | 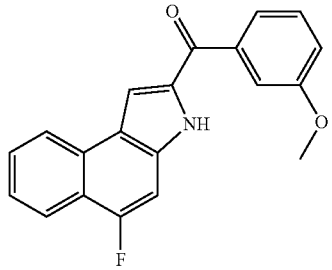 [SMILES: COc1cccc(C(=O)c2cc3c(cc(F)c4ccccc43)[nH]2)c1]<br>(5-Fluoro-3H-benzo[e]indol-2-yl)-(3-methoxy-phenyl)-methanone. The compound may be prepared using Scheme 1. $^1$H NMR (300 MHz, DMSO-d$_6$) δ 12.50 (s, 1 H), 8.50 (d, J = 8.4 Hz, 1 H), 8.07 (d, J = 7.8 Hz, 1 H), 7.87 (brs, 1 H), 7.72-7.65 (m, 1 H), 7.59-7.54 (m, 3 H), 7.45-7.38 (m, 2 H), 7.29-7.26 (m, 1 H), 3.88 (s, 3 H). |
| ACT-PFK-118 | 290.29 | 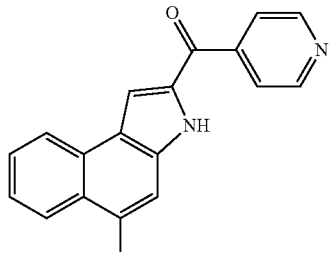<br>(5-Fluoro-3H-benzo[e]indol-2-yl)-pyridin-4-yl-methanone. The compound may be prepared using Scheme 1. $^1$H NMR (300 MHz, DMSO-d$_6$) δ 12.64 (s, 1 H), 8.86 (d, J = 4.8 Hz, 2 H), 8.49 (d, J = 8.1 Hz, 1 H), 8.08 (d, J = 8.1 Hz, 1 H), 7.93-7.85 (m, 3 H), 7.71-7.68 (m, 1 H), 7.61-7.58 (m, 1 H), 7.40 (d, J = 10.8 Hz, 1 H). |
| ACT-PFK-117 | 425.5 | 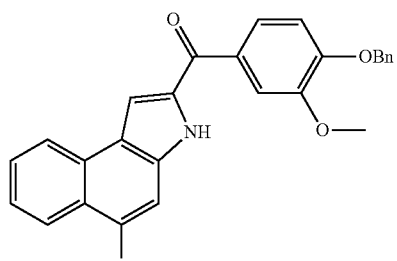<br>(4-Benzyloxy-3-methoxy-phenyl)-(5-fluoro-3H-benzo[e]indol-2-yl)-methanone. The compound may be prepared using Scheme 1. $^1$H NMR (300 MHz, DMSO-d$_6$) δ 12.41 (s, 1 H), 8.50 (d, J = 7.8 Hz, 1 H), 8.07(d, J = 7.8 Hz, 1H), 7.89 (br s, 1 H), 7.72-7.69 (m. 2H), 7.59-7.38 (m, 8 H), 7.26 (d, J = 8.4 Hz, 1H), 5.25 (s, 2H), 3.90 (s, 3H). |

TABLE 1-continued

Exemplary Compounds

| Compound Number | Mw | Structure, Name and NMR Data |
|---|---|---|
| ACT-PFK-119 | 335.33 | 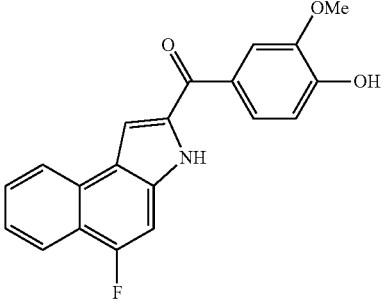 [SMILES: COc1cc(C(=O)c2cc3c(cc(F)c4ccccc43)[nH]2)ccc1O]<br>(5-Fluoro-3H-benzo[e]indol-2-yl)-(4-hydroxy-3-methoxy-phenyl)-methanone. The compound may be prepared using Scheme 1. $^1$H NMR (300 MHz, DMSO-d$_6$) δ 12.37 (s, 1 H), 9.99 (s, 1 H), 8.50 (d, J = 8.1 Hz, 1 H), 8.07 (d, J = 8.1 Hz, 1 H), 7.88 (d, J = 1.8 Hz, 1 H), 7.72-7.52 (m, 4 H), 7.39 (d, J = 11.1 Hz, 1 H), 6.99 (d, J = 8.1 Hz, 1 H), 3.90 (s, 3 H). |
| ACT-PFK-120 | 301.3 | 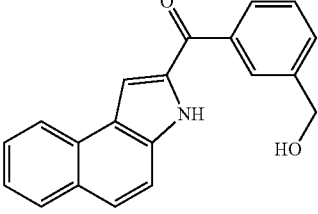<br>(3H-Benzo[e]indol-2-yl)-(3-hydroxymethyl-phenyl)-methanone. The compound may be prepared using Scheme 1. $^1$H NMR (300 MHz, DMSO-d$_6$) δ 12.46 (s, 1 H), 8.36 (d, J = 7.8 Hz, 1 H), 8.09-7.94 (m, 3H), 7.81-7.78 (m, 3H), 7.71-7.58 (m. 3H), 7.47 (d, J = 7.5 Hz, 1 H), 5.60 (s, 2H). |
| ACT-PFK-121 | 295.4 | 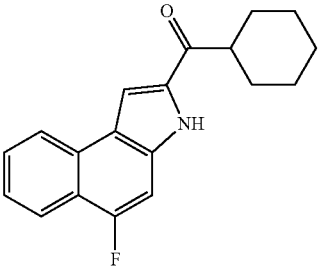 [SMILES: O=C(c1cc2c(cc(F)c3ccccc32)[nH]1)C1CCCCC1]<br>Cyclohexyl-(5-fluoro-3H-benzo[e]indol-2-yl)-methanone. The compound may be prepared using Scheme 1. $^1$H NMR (300 MHz, DMSO-d$_6$) δ 12.16 (s, 1 H), 8.45 (d, J = 8.7 Hz, 1 H), 8.12 (s, 1H), 8.05 (d, J = 8.10 Hz, 1H), 7.71 (t, J = 7.50 Hz. 1H), 7.56 (t, J = 7.50 Hz. 1H), 7.33 (d, J = 11.4 Hz, 1H), 1.95-1.68 (m, 5H), 1.56-1.37 (m, 4H), 1.34-1.17 (m, 1H). |

TABLE 1-continued

Exemplary Compounds

| Compound Number | Mw | Structure, Name and NMR Data |
|---|---|---|
| ACT-PFK-122 | 323.3 | 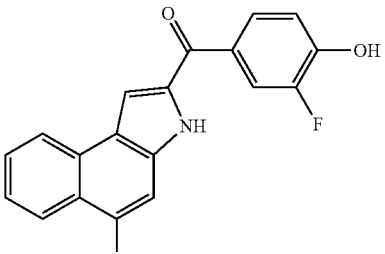<br>(5-Fluoro-3H-benzo[e]indol-2-yl)-(3-fluoro-4-hydroxy-phenyl)-methanone. The compound may be prepared using Scheme 1. $^1$H NMR (300 MHz, DMSO-$d_6$) δ 12.41 (s, 1 H), 10.99 (s, 1H), 8.51 (d, J = 8.1 Hz, 1 H), 8.07 (d, J = 8.1 Hz, 1 H), 7.92 (s, 1H), 7.80-7.68 m, 3H), 7.59-7.55 (m, 1 H), 7.38 (d, J = 11.1 Hz, 1 H), 7.19-7.13 (m, 1H). |
| ACT-PFK-123 | 285.3 | 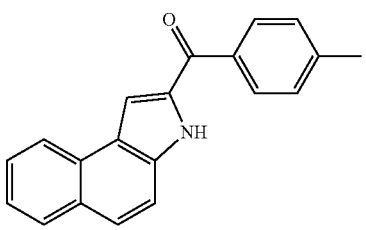 [SMILES: Cc1ccc(C(=O)c2cc3c(ccc4ccccc43)[nH]2)cc1]<br>(3H-Benzo[e]indol-2-yl)-p-tolyl-methanone. The compound may be prepared using Scheme 1. $^1$H NMR (300 MHz, DMSO-$d_6$) δ 12.44 (s, 1 H), 8.39 (d, J = 7.8. Hz, 1 H), 7.09-7.96 (m, 3H), 7.56-7.80 (m, 2 H), 7.57-7.64 (m. 2H), 7.42-7.45 (m, 3 H), 2.46 (s, 3H). |
| ACT-PFK-124 | $C_{20}H_{17}NO_2$<br>Mol. Wt.:<br>303.4 | 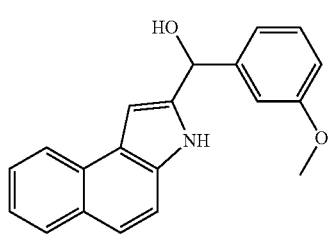 [SMILES: COc1cccc(C(O)c2cc3c(ccc4ccccc43)[nH]2)c1]<br>(3H-Benzo[e]indol-2-yl)-(3-methoxy-phenyl)-methanol. $^1$H NMR (300 MHz, DMSO-$d_6$) δ 11.40 (s, 1 H), 8.13 (d, J = 6.0. Hz, 1 H), 7.69 (d, J = 7.8 Hz, 1 H), 7.54-7.42 (m, 3 H), 7.35-7.23 (m. 2H), 7.12-7.04 (m, 2 H), 6.84-6.79 (m, 2 H), 6.13 (d, J = 4.2, 1 H), 5.91 (d, J = 3.9, 1H), 3.75 (s, 3H). |
| ACT-PFK-125 | $C_{18}H_{14}N_2O$<br>Mol. Wt.:<br>274.3 | 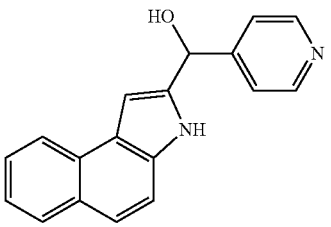 [SMILES: OC(c1ccncc1)c1cc2c(ccc3ccccc32)[nH]1]<br>(3H-Benzo[e]indol-2-yl)-pyridin-4-yl-methanol. $^1$H NMR (300 MHz, DMSO-$d_6$) δ 11.50 (s, 1 H), 8.55 (d, J = 4.8. Hz, 2 H), 8.14 (d, J = 8.1 Hz, 1 H), 7.86 (d J = 7.8, 1 H), 7.55-7.44 (m. 5 H), 7.36-7.31 (m, 1 H), 6.84 (s, 1 H), 6.39 (br s, 1 H), 5.97 (s, 1H). |

TABLE 1-continued

Exemplary Compounds

| Compound Number | Mw | Structure, Name and NMR Data |
|---|---|---|
| ACT-PFK-126 | $C_{19}H_{14}N_2O$<br>Mol. Wt.:<br>286.3 | 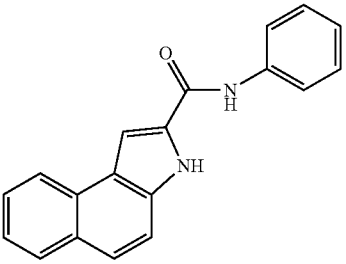 [SMILES: O=C(Nc1ccccc1)c1cc2c(ccc3ccccc32)[nH]1]<br>3H-Benzo[e]indole-2-carboxylic acid phenylamide. $^1$H NMR (300 MHz, DMSO-d$_6$) δ 12.22 (s, 1 H), 10.28 (s, 1 H), 8.23 (d, J = 7.8. Hz, 1 H), 8.01-7.94 (m, 2 H), 7.86-7.83 (m, 2 H), 7.71-7.59 (m. 3 H), 7.47-7.37 (m, 3 H), 7.14-7.09 (m, 1 H). |
| ACT-PFK-127 | $C_{20}H_{16}N_2O_2$<br>Mol. Wt.:<br>316.4 | 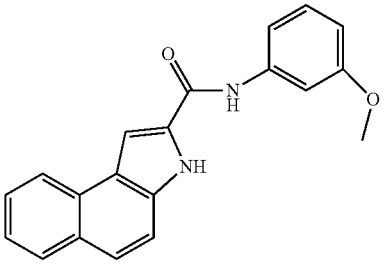 [SMILES: COc1cccc(NC(=O)c2cc3c(ccc4ccccc43)[nH]2)c1]<br>3H-Benzo[e]indole-2-carboxylic acid (3-methoxy-phenyl)-amide. $^1$H NMR (300 MHz, DMSO-d$_6$) δ 12.22 (s, 1 H), 10.24 (s, 1 H), 8.23 (d, J = 6.3. Hz, 1 H), 8.00-7.94 (m, 2 H), 7.71-7.68 (m, 1 H), 7.63-7.58 (m. 2 H), 7.52 (s, 1 H), 7.45-7.43 (m, 2 H), 7.32-7.26 (m, 1 H), 6.71-6.68 (m, 1 H), 3.79 (s, 3 H). |
| ACT-PFK-128 | $C_{21}H_{18}N_2O$<br>Mol. Wt.:<br>314.4 | 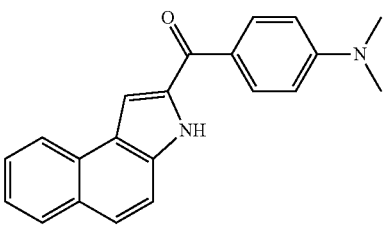 [SMILES: CN(C)c1ccc(C(=O)c2cc3c(ccc4ccccc43)[nH]2)cc1]<br>(3H-Benzo[e]indol-2-yl)-(4-dimethylamino-phenyl)-methanone. $^1$H NMR (300 MHz, DMSO-d$_6$) δ 12.22 (s, 1 H), 8.39-8.37 (m, 1 H), 7.99-7.92 (m, 3 H), 7.79-7.72 (m, 2 H), 7.64-7.54 (m, 2 H), 7.46-7.44 (m. 1 H), 6.87-6.84 (m, 2 H), 3.31 (s, 6 H). |
| ACT-PFK-129 | $C_{20}H_{16}N_2O_2$<br>Mol. Wt.:<br>316.4 | 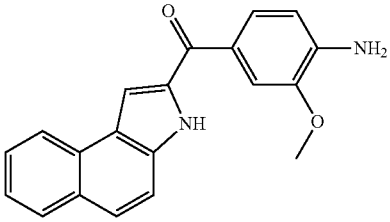 [SMILES: COc1cc(C(=O)c2cc3c(ccc4ccccc43)[nH]2)ccc1N]<br>(4-Amino-3-methoxy-phenyl)-(3H-benzo[e]indol-2-yl)-methanone. $^1$H NMR (300 MHz, DMSO-d$_6$) δ 12.29 (s, 1 H), 8.36 (d, J = 8.1 Hz, 1 H), 7.93 (d, J = 8.1 Hz, 1 H), 7.74 (d, J = 8.7 Hz, 1 H), 7.65-7.54 (m, 4 H), 7.47-7.42 (m. 1 H), 7.05 (d, J = 8.1 Hz, 1 H), 6.73-6.68 (m, 1 H), 6.35 (s, 2 H), 3.88 (s, 3 H). |

TABLE 1-continued

Exemplary Compounds

| Compound Number | Mw | Structure, Name and NMR Data |
|---|---|---|
| ACT-PFK-130 | C<sub>20</sub>H<sub>16</sub>N<sub>2</sub>O<sub>3</sub><br>Mol. Wt.:<br>332.4 | 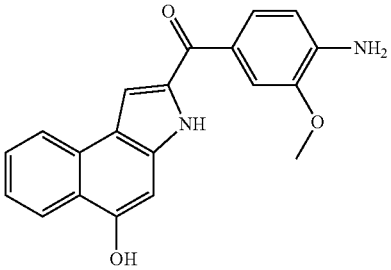 [SMILES: COc1cc(C(=O)c2cc3c(cc(O)c4ccccc43)[nH]2)ccc1N]<br>(4-Amino-3-methoxy-phenyl)-(5-hydroxy-3H-benzo[e]indol-2-yl)-methanone. $^1$H NMR (300 MHz, DMSO-d$_6$) δ 11.90 (s, 1 H), 10.34 (s, 1 H), 8.25 (d, J = 8.1 Hz, 1 H), 8.15 (d, J = 8.1 Hz, 1 H), 7.56-7.45 (m, 3 H), 7.43-7.38 (m, 1 H), 7.07-7.01 (m, 2 H), 6.71-6.66 (m, 1 H), 6.14 (s, 2 H), 3.87 (s, 3 H). |
| ACT-PFK-131 | C<sub>21</sub>H<sub>18</sub>N<sub>2</sub>O<sub>3</sub><br>Mol. Wt.:<br>346.4 | 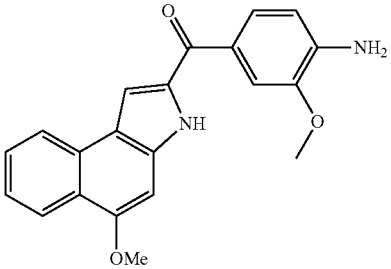 [SMILES: COc1cc(C(=O)c2cc3c(cc(OC)c4ccccc43)[nH]2)ccc1N]<br>(4-Amino-3-methoxy-phenyl)-(5-methoxy-3H-benzo[e]indol-2-yl)-methanone. $^1$H NMR (300 MHz, DMSO-d$_6$) δ 12.09 (s, 1 H), 8.30 (d, J = 8.1 Hz, 1 H), 8.17 (d, J = 8.1 Hz, 1 H), 7.60-7.53 (m, 3 H), 7.46-7.40 (m, 1 H), 7.08-7.00 (m, 2 H), 6.72-6.69 (m, 1 H), 6.20 (s, 2 H), 4.02 (s, 3 H), 3.87 (s, 3 H). |
| ACT-PFK-133 | C<sub>20</sub>H<sub>16</sub>N<sub>2</sub>O<sub>3</sub>S<br>Mol. Wt.:<br>364.4 | 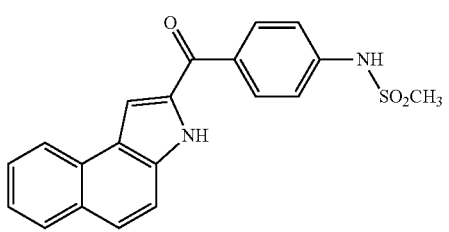 [SMILES: CS(=O)(=O)Nc1ccc(C(=O)c2cc3c(ccc4ccccc43)[nH]2)cc1]<br>N-[4-(3H-Benzo[e]indole-2-carbonyl)-phenyl]-methanesulfonamide. $^1$H NMR (300 MHz, DMSO-d$_6$) δ 12.38 (s, 1 H), 10.37 (s, 1 H), 8.41 (d, J = 8.1 Hz, 1 H), 8.05-7.93 (m, 3 H), 7.85-7.75 (m, 2 H), 7.64-7.55 (m, 2 H), 7.45-7.40 (m. 3 H), 3.33 (s, 3 H). |
| ACT-PFK-134 | C<sub>19</sub>H<sub>15</sub>N<sub>3</sub>O<br>Mol. Wt.:<br>301.3 | 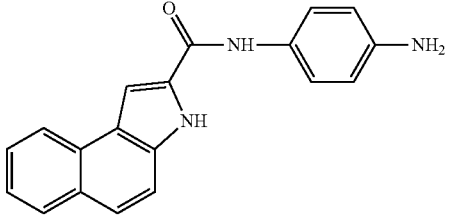 [SMILES: Nc1ccc(NC(=O)c2cc3c(ccc4ccccc43)[nH]2)cc1]<br>3H-Benzo[e]indole-2-carboxylic acid (4-amino-phenyl)-amide. $^1$H NMR (300 MHz, DMSO-d$_6$) δ 12.09 (s, 1 H), 9.92 (s, 1 H), 8.19 (d, J = 8.1 Hz, 1 H), 7.95-7.91 (m, 2 H), 7.68-7.57 (m, 3 H), 7.44-7.42 (m, 3 H), 6.58 (d, J = 8.1 Hz, 2 H), 4.95 (s, 2 H). |

TABLE 1-continued

Exemplary Compounds

| Compound Number | Mw | Structure, Name and NMR Data |
|---|---|---|
| ACT-PFK-135 | C₂₀H₁₆N₂O₂ Mol. Wt.: 316.4 | 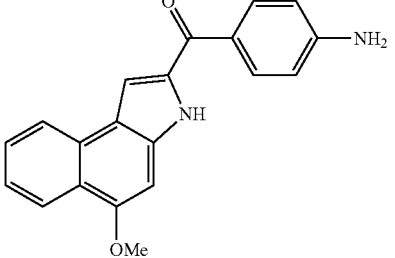<br>(4-Amino-phenyl)-(5-methoxy-3H-benzo[e]indol-2-yl)-methanone. ¹H NMR (300 MHz, DMSO-d₆) δ 11.99 (s, 1H), 8.34 (d, J = 8.1 Hz, 1H), 8.16 (d, J = 8.1 Hz, 1H), 7.82 (d, J = 8.1 Hz, 2H), 7.68 (s, 1H), 7.61-7.56 (m, 1H), 7.46-7.41 (m, 1H), 7.00 (s, 1 H), 6.68 (d, J = 8.4 Hz,, 2H), 6.02 (s, 2H), 4.01 (s, 3H). |
| ACT-PFK-136 | C₂₀H₁₅FN₂O₂ Mol. Wt.: 334.3 | 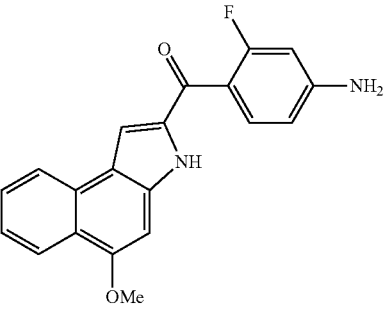 [SMILES: COc1cc2[nH]c(C(=O)c3ccc(N)cc3F)cc2c2ccccc12]<br>(4-Amino-2-fluoro-phenyl)-(5-methoxy-3H-benzo[e]indol-2-yl)-methanone. ¹H NMR (300 MHz, DMSO-d₆) δ 12.05 (s, 1H), 8.37 (d, J = 6.3 Hz, 1H), 8.17 (d, J = 8.7 Hz, 1H), 7.76-7.57 (m, 4H), 7.47-7.44(m, 1H), 6.99-6.89 (m, 2H), 6.09 (s, 2H), 4.01 (s, 3H). |
| ACT-PFK-137 | C₂₀H₁₅FN₂O₂ Mol. Wt.: 334.3 | 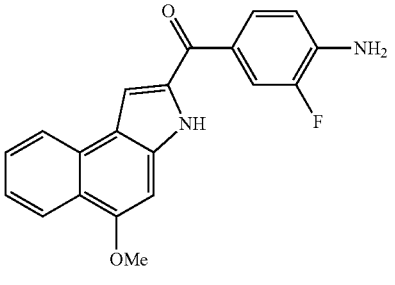 [SMILES: COc1cc2[nH]c(C(=O)c3ccc(N)c(F)c3)cc2c2ccccc12]<br>(4-Amino-3-fluoro-phenyl)-(5-methoxy-3H-benzo[e]indol-2-yl)-methanone |
| ACT-PFK-138 | C₂₁H₁₈N₂O₃ Mol. Wt.: 346.4 | 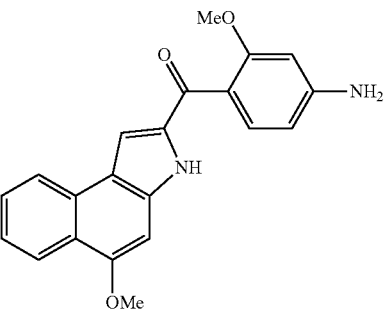 [SMILES: COc1cc(N)ccc1C(=O)c1cc2c(cc(OC)c3ccccc32)[nH]1]<br>(4-Amino-2-methoxy-phenyl)-(5-methoxy-3H-benzo[e]indol-2-yl)-methanone |

TABLE 1-continued

Exemplary Compounds

| Compound Number | Mw | Structure, Name and NMR Data |
|---|---|---|
| ACT-PFK-139 | $C_{20}H_{16}N_2O_2$<br>Mol. Wt.:<br>316.4 | 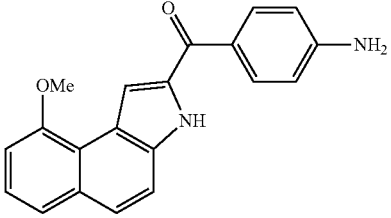 [SMILES: COc1cccc2ccc3[nH]c(C(=O)c4ccc(N)cc4)cc3c12]<br>(4-Amino-phenyl)-(9-methoxy-3H-benzo[e]indol-2-yl)-methanone |
| ACT-PFK-140 | $C_{21}H_{18}N_2O_3$<br>Mol. Wt.:<br>346.4 | <br>(4-Amino-3-methoxy-phenyl)-(9-methoxy-3H-benzo[e]indol-2-yl)-methanone |
| ACT-PFK-141 | $C_{21}H_{18}N_2O_3$<br>Mol. Wt.:<br>346.4 | 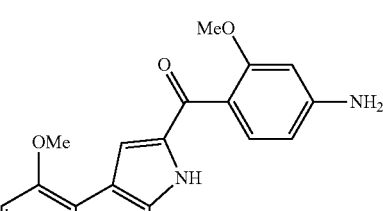<br>(4-Amino-2-methoxy-phenyl)-(9-methoxy-3H-benzo[e]indol-2-yl)-methanone |
| ACT-PFK-142 | $C_{20}H_{15}FN_2O_2$<br>Mol. Wt.:<br>334.3 | 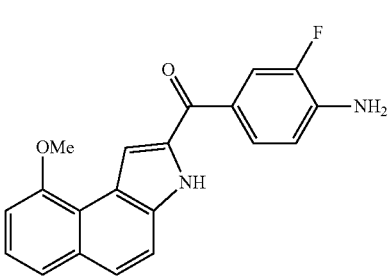 [SMILES: COc1cccc2ccc3[nH]c(C(=O)c4ccc(N)c(F)c4)cc3c12]<br>(4-Amino-3-fluoro-phenyl)-(9-methoxy-3H-benzo[e]indol-2-yl)-methanone |
| ACT-PFK-143 | $C_{20}H_{15}FN_2O_2$<br>Mot. Wt.:<br>334.3 | 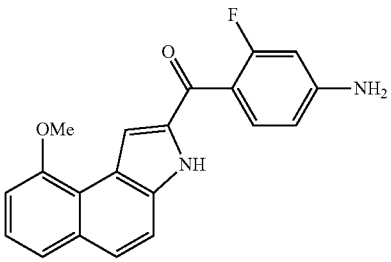 [SMILES: COc1cccc2ccc3[nH]c(C(=O)c4ccc(N)cc4F)cc3c12]<br>(4-Amino-2-fluoro-phenyl)-(9-methoxy-3H-benzo[e]indol-2-yl)-methanone |

TABLE 1-continued

Exemplary Compounds

| Compound Number | Mw | Structure, Name and NMR Data |
|---|---|---|
| ACT-PFK-144 | C₁₉H₁₃FN₂O Mol. Wt.: 304.3 | 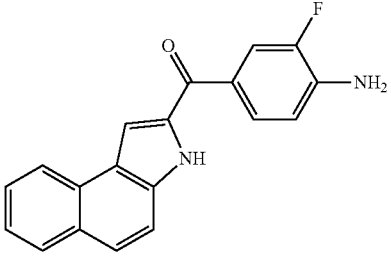 [SMILES: Nc1ccc(C(=O)c2cc3c(ccc4ccccc43)[nH]2)cc1F] (4-Amino-3-fluoro-phenyl)-(3H-benzo[e]indol-2-yl)-methanone |
| ACT-PFK-145 | C₁₉H₁₃FN₂O Mol. Wt.: 304.3 | 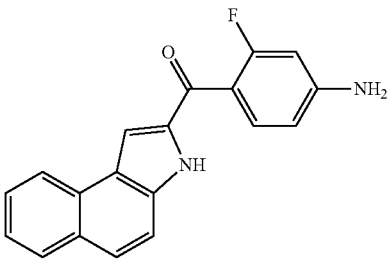 [SMILES: Nc1ccc(C(=O)c2cc3c(ccc4ccccc43)[nH]2)c(F)c1] (4-Amino-2-fluoro-phenyl)-(3H-benzo[e]indol-2-yl)-methanone |
| ACT-PFK-146 | C₂₀H₁₆N₂O₂ Mol. Wt.: 316.4 | 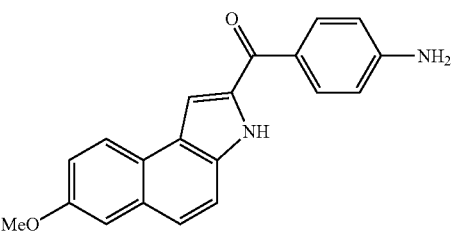 [SMILES: COc1ccc2c(ccc3[nH]c(C(=O)c4ccc(N)cc4)cc32)c1] (4-Amino-phenyl)-(7-methoxy-3H-benzo[e]indol-2-yl)-methanone |
| ACT-PFK-147 | C₂₀H₁₆N₂O₂ Mol. Wt.: 316.4 | 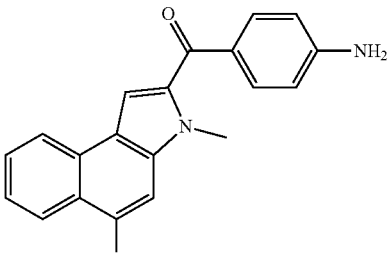 (4-Amino-phenyl)-(5-hydroxy-3-methyl-3H-benzo[e]indol-2-yl)-methanone |

TABLE 1-continued

Exemplary Compounds

| Compound Number | Mw | Structure, Name and NMR Data |
|---|---|---|
| ACT-PFK-148 | C$_{19}$H$_{14}$FN$_3$O$_2$<br>Mol. Wt.:<br>335.3 | 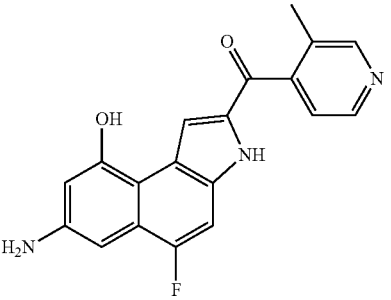 [SMILES: Cc1cnccc1C(=O)c1cc2c(cc(F)c3cc(N)cc(O)c32)[nH]1]<br>(7-Amino-5-fluoro-9-hydroxy-3H-benzo[e]indol-2-yl)-(3-methyl-pyridin-4-yl)-methanone |
| ACT-PFK-149 | C$_{18}$H$_{14}$N$_4$O$_2$<br>Mol. Wt.:<br>318.3 | 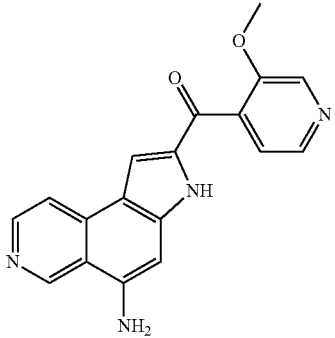 [SMILES: COc1cnccc1C(=O)c1cc2c(cc(N)c3cnccc32)[nH]1]<br>(5-Amino-3H-pyrrolo[3,2-f]isoquinolin-2-yl)-(3-methoxy-pyridin-4-yl)-methanone |
| ACT-PFK-150 | C$_{19}$H$_{15}$N$_3$O$_2$<br>Mol. Wt.:<br>317.3 | 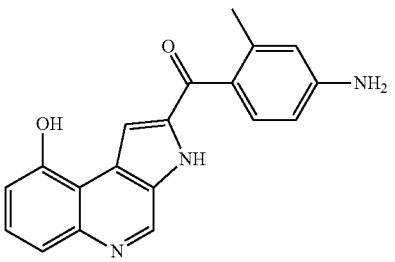 [SMILES: Cc1cc(N)ccc1C(=O)c1cc2c(cnc3cccc(O)c32)[nH]1]<br>(4-Amino-2-methyl-phenyl)-(9-hydroxy-3H-pyrrolo[2,3-c]quinolin-2-yl)-methanone |
| ACT-PFK-151 | C$_{20}$H$_{16}$N$_2$O$_3$S<br>Mol. Wt.:<br>364.4 | 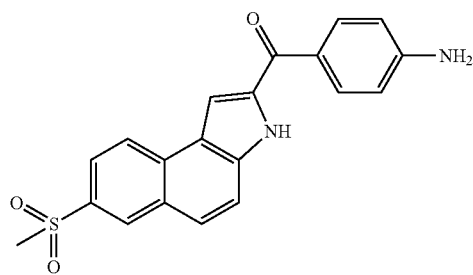 [SMILES: CS(=O)(=O)c1ccc2c(ccc3[nH]c(C(=O)c4ccc(N)cc4)cc32)c1]<br>(4-Amino-phenyl)-(7-methanesulfonyl-3H-benzo[e]indol-2-yl)-methanone |

II. Chemical Synthesis

Formula I compounds of the present invention are prepared using the general method described below in Scheme I, together with synthetic methods known by one in the art of organic synthesis and variations thereon. One skilled in the art will appreciate that aryl and naphthyl moieties may be unsubstituted or substituted with any number of suitable substituents. Such variations are within the purview of the ordinary skilled artisan

Scheme 1

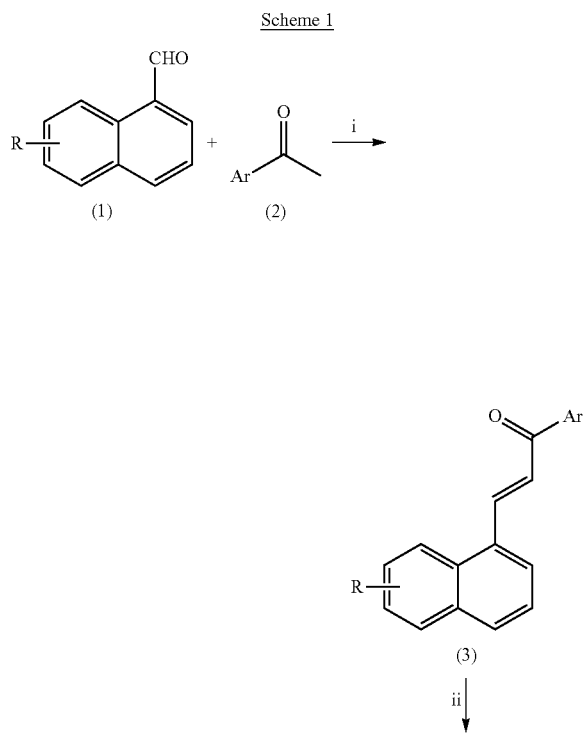

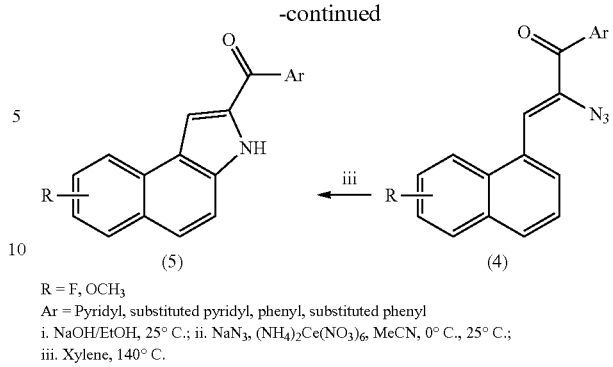

R = F, OCH$_3$
Ar = Pyridyl, substituted pyridyl, phenyl, substituted phenyl
i. NaOH/EtOH, 25° C.; ii. NaN$_3$, (NH$_4$)$_2$Ce(NO$_3$)$_6$, MeCN, 0° C., 25° C.;
iii. Xylene, 140° C.

Referring to step (i) of Scheme 1, 1-naphthaldehyde or substituted 1-naphthaldehyde is reacted with aryl methyl ketone under basic conditions from 0° C. to 100° C. to produce corresponding chalcones. Substituted naphthaldehydes and substituted aryl methyl ketones are purchased from commercial sources or prepared according to literature procedures. In step (ii), the chalcones so produced are further reacted with an azide source in the presence of ceric ammonium nitrate at 0° C. to 100° C. and then in step (iii), thermal cyclization at 50° C. to 200° C. of the azido compound in an appropriate solvent gives the desired substituted benzindoles.

In another embodiment, Formula I compounds of the present invention are also prepared using the method described below in Scheme 2, together with synthetic methods known by one in the art of organic synthesis and variations thereon. One skilled in the art will appreciate that phenyl and naphthyl moieties may be unsubstituted or substituted with any number of suitable substituents. Such variations are within the purview of the ordinary skilled artisan.

Scheme 2

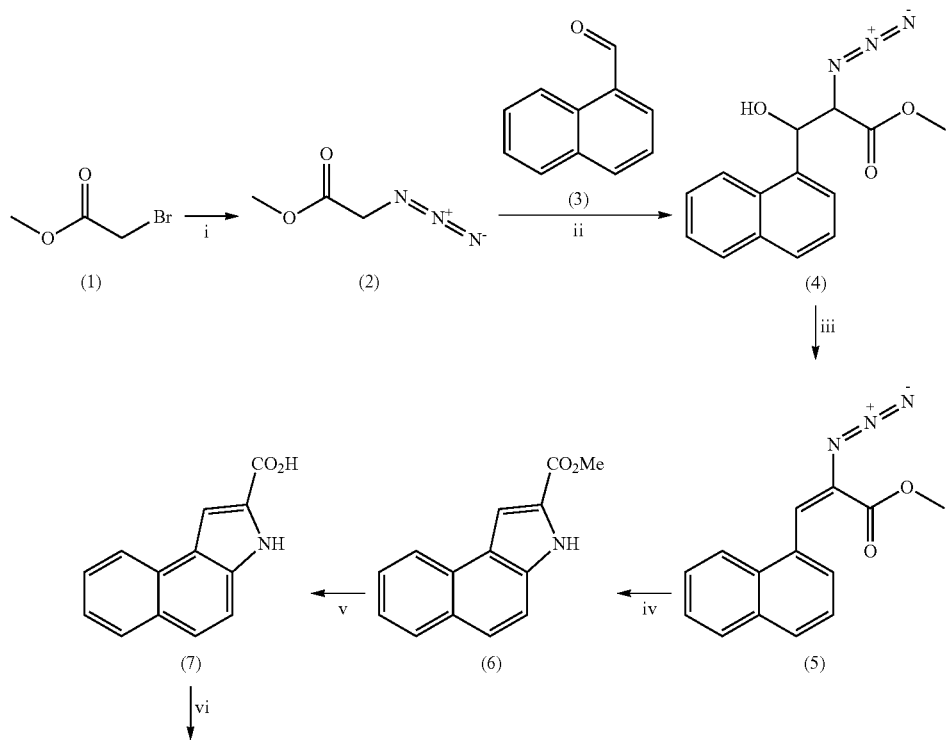

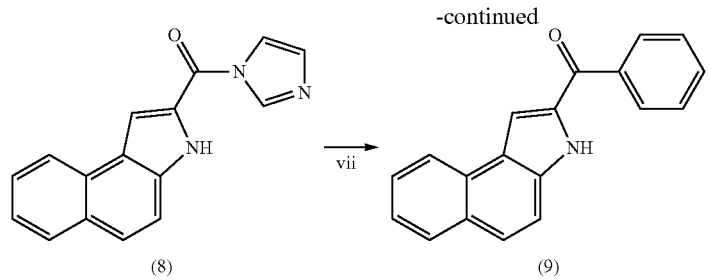

i. NaN₃, DMF, 25° C., ii. NaOMe, MeOH, 30° C., iii. Et₃N, MeSO₂Cl, DCM, -40° C., iv. Xylene, 140° C., v. 1N NaOH, MeOH, Acetone, 25° C., vii. N,N'-carbonyldiimidazole, THF, 25° C., vii. PhMgBr, THF, 0° C., 25° C.

The compounds of Formula (I) can also be prepared using above Scheme 2, wherein substituted or unsubstituted 1-naphthaldehyde (3) is reacted with azidomethyl ester (2) under basic conditions at 0° C. to 100° C. to produce compound (4). The elimination of hydroxyl group is achieved through the formation of methanesulphonyl derivative followed by cyclization with heating at 100° C. to 200° C. to give compound (6). Further basic hydrolysis of ester (6) results in the corresponding acid (7) which is reacted with N,N'-carbonyldiimidazole to yield amide (8). The displacement of imidazole moiety with corresponding aryl magnesium bromide produces the desired target (9).

In a specific embodiment, compound ACT-PFK-095 and its analogs are prepared using the method described below in Scheme 3, together with synthetic methods known by one in the art of organic synthesis and variations thereon:

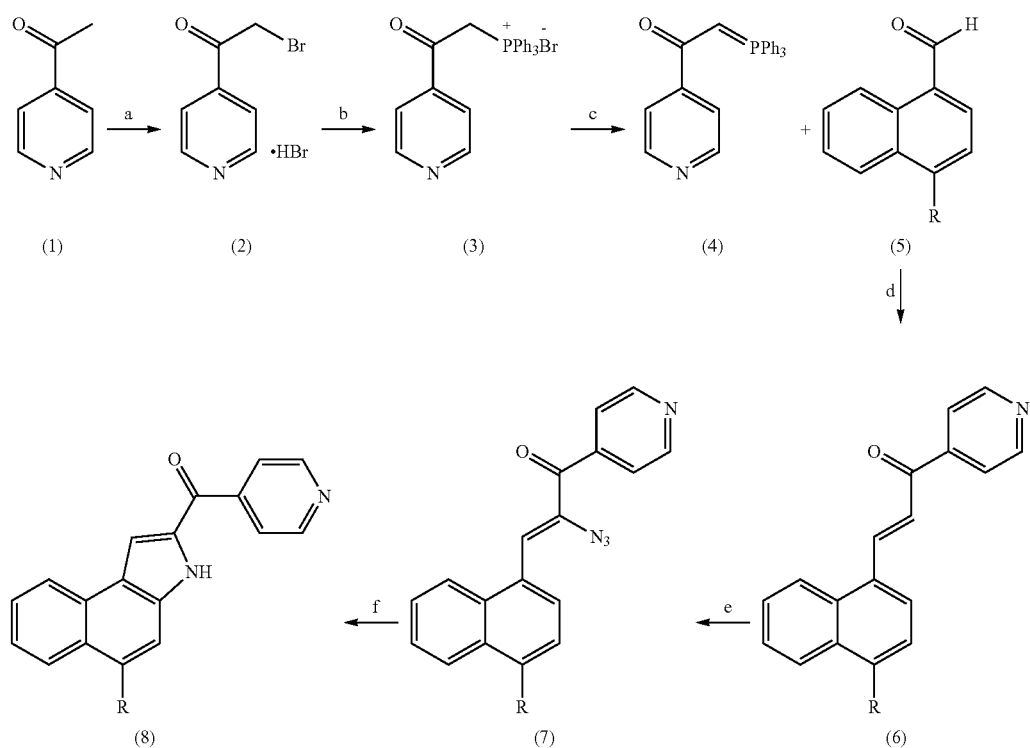

R = H, F
(a) Br₂, CCl₄; (b) PPh₃, Et₃N, THF; (c) 3N NaOH, MeOH; (d) toluene, reflux; (e) NaN₃, (NH₄)₂Ce(NO₃)₆, MeCN, 0° C., 25° C.; (f) xylene, 140° C.

In another specific embodiment, compound ACT-PFK-112 and its analogs are prepared using the method described below in Scheme 4, together with synthetic methods known by one in the art of organic synthesis and variations thereon:

Scheme 4

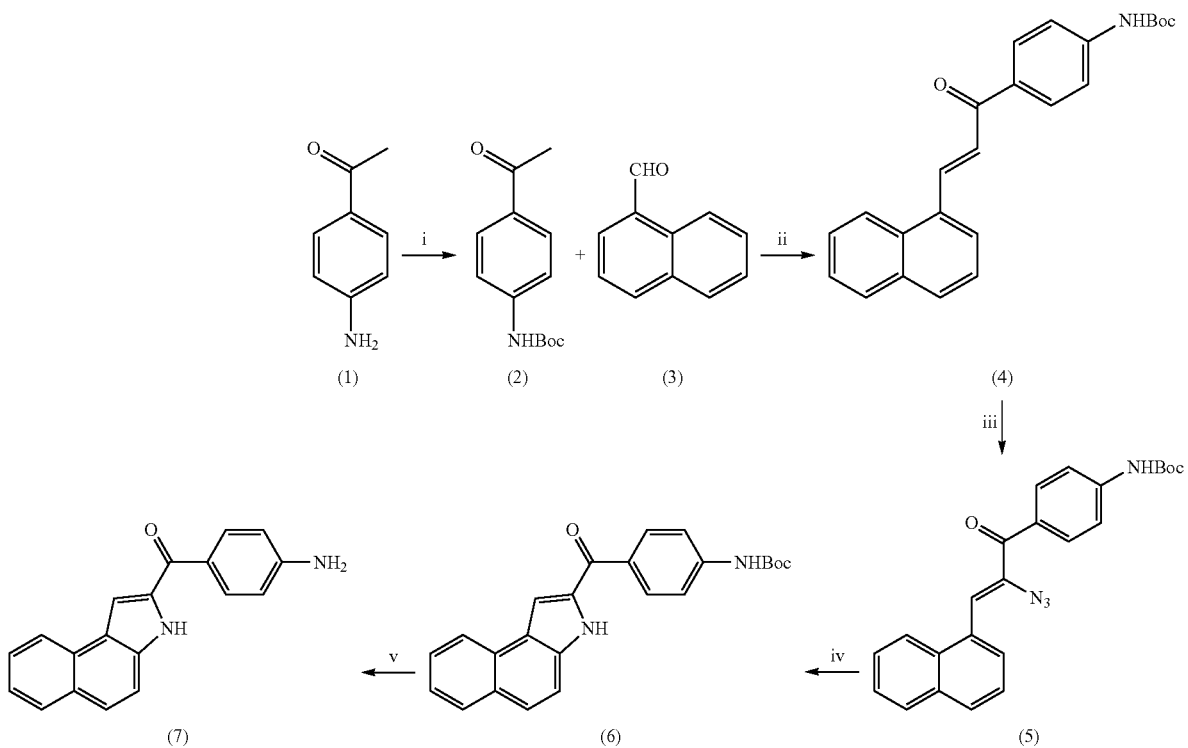

i. Boc anhydride, THF, 25° C.; ii. NaOH, H₂O—EtOH, 25° C.; iii. NaN₃, (NH₄)₂Ce(NO₃)₆, MeCN, 0° C., 25° C.; iv. xylene, 140° C.; v. HCl, dioxane, 25° C.

In another embodiment, Formula II compounds of the present invention are prepared using the method described below in Scheme 5, together with synthetic methods known by one in the art of organic synthesis and variations thereon. One skilled in the art will appreciate that phenyl and naphthyl rings may be unsubstituted or substituted with any number of suitable substituents. Such variations are within the purview of the ordinary skilled artisan.

Scheme 5

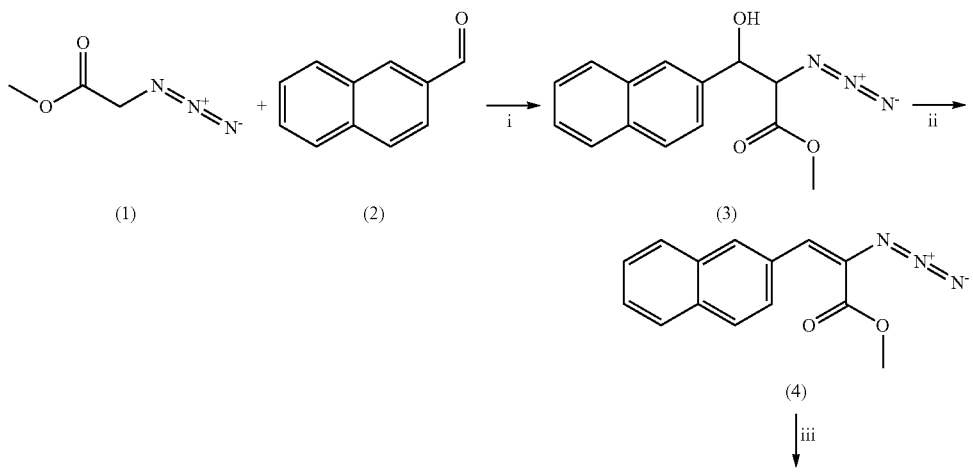

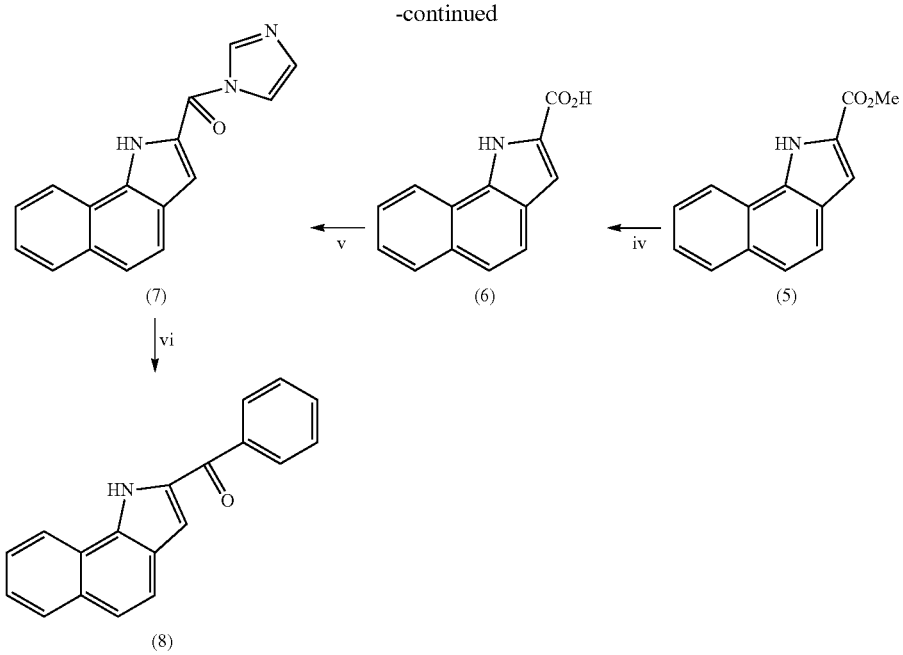

i. NaOMe, MeOH, -20° C., -15° C., ii. Et₃N, MeSO₂Cl, DCM, -40° C., iii. Xylene, 140° C., iv. 1N NaOH, MeOH, Acetone, 25° C., v. N,N'-cabonyldiimidazole, THF, 25° C., vi. PhMgBr, THF, 0° C.

III. Pharmaceutical Compositions

The compounds of Formula I, Formula II, and Formula III, including tautomeric, enantiomeric or diastereomeric forms and pharmaceutically acceptable salts, prodrugs, or metabolites thereof, are all referred to herein as "anti-cancer compounds." The compounds disclosed herein can be administered to a subject either alone, or as part of a pharmaceutical composition.

Pharmaceutical compositions comprising the aforementioned anti-cancer compounds also are provided herein. These pharmaceutical compositions comprise active compounds as described herein, in a pharmaceutically acceptable carrier. Pharmaceutical formulations can be prepared for oral, intravenous, parenteral, or aerosol administration as discussed in greater detail below. Also, the compounds of the present invention provide such anti-cancer compounds that can be reconstituted to form pharmaceutically acceptable compositions (including compositions pharmaceutically acceptable in humans) for administration.

The term "carrier," as used herein, includes pharmaceutically acceptable carriers, excipients, or stabilizers which are nontoxic to the cell or mammal being exposed thereto at the dosages and concentrations employed.

The therapeutically effective dosage of any specific anti-cancer compound, the use of which is within the scope of embodiments described herein, will vary somewhat from compound to compound, and subject to subject, and will depend upon the condition of the subject and the route of delivery. As a general proposition, a dosage from about 0.1 to about 500 mg/kg will have therapeutic efficacy, with all weights being calculated based upon the weight of the active compound, including the cases where a salt is employed.

In accordance with the presently disclosed methods, pharmaceutically active compounds as described herein can be administered orally as a solid, liquid, or gel, or can be administered intramuscularly or intravenously as a solution, suspension, or emulsion. Alternatively, the compounds or salts also can be administered by inhalation, intravenously, or intramuscularly as a liposomal suspension. When administered through inhalation the active compound or salt should be in the form of a plurality of solid particles or droplets having a particle size from about 0.5 to about 5 microns, and preferably from about 1 to about 2 microns.

Pharmaceutical compositions suitable for intravenous or intramuscular injection are further embodiments provided herein. The pharmaceutical compositions comprise a compound of Formula I, Formula II, or Formula III described herein, including tautomeric, enantiomeric or diastereomeric forms and pharmaceutically acceptable salts, prodrugs, or metabolites thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formula I, Formula II, or Formula III, including tautomeric, enantiomeric or diastereomeric forms and pharmaceutically acceptable salts, prodrugs, or metabolites thereof, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical compositions described herein can be lyophilized using techniques well known in the art.

In yet another embodiment of the subject matter described herein, there is provided an injectable, stable, sterile formulation comprising a compound of Formula I, Formula II, Formula III, or a tautomeric, enantiomeric or diastereomeric form or pharmaceutically acceptable salt, prodrug, or metabolites thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier.

Other pharmaceutical compositions can be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof.

Additional embodiments provided herein include liposomal formulations of the active compounds disclosed herein. The technology for forming liposomal suspensions is well known in the art.

Pharmaceutical compositions also are provided which are suitable for administration as an aerosol by inhalation. These compositions comprise a solution or suspension of a desired compound described herein or a salt thereof, or a plurality of solid particles of the compound or salt. The desired composition can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns.

As indicated, both water-soluble and water-insoluble active compounds are provided. As used herein, the term "water-soluble" is meant to define any composition that is soluble in water in an amount of about 10 mg/mL, or greater. Also, as used herein, the term "water-insoluble" is meant to define any composition that has solubility in water of less than about 1 mg/mL. In some embodiments, water-soluble compounds or salts can be desirable whereas in other embodiments water-insoluble compounds or salts likewise can be desirable.

IV. Methods of Inhibiting Cell Proliferation and Treating Cancer

The compounds of the present invention and compositions including them are useful for inhibiting cell proliferation and/or treating cancer.

In some embodiments, the methods for inhibiting cell proliferation or treating a cancer comprise administering to a subject in need thereof an anti-cancer compound as described herein. These active compounds, as set forth above, include the compounds of Formula I, Formula II, and Formula III, including tautomeric, enantiomeric or diastereomeric forms and pharmaceutically acceptable salts, prodrugs, or metabolites thereof. In some embodiments, the active compound is present in a pharmaceutical formulation as described hereinabove.

The presently disclosed compounds can provide therapy for a wide variety of tumors and cancers including skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood, and lymphoid cancers.

An "effective amount" as defined herein in relation to the treatment of cancers is an amount that will decrease, reduce, inhibit, or otherwise abrogate the growth of a cancer cell or tumor. In some embodiments, the compound of Formula I, Formula II, or Formula III can be delivered regionally to a particular affected region or regions of the subject's body. In some embodiments, wherein such treatment is considered more suitable, the compound can be administered systemically. For example, the compound can be administered orally or intravenously.

In addition, it will be appreciated that therapeutic benefits for the treatment of cancer can be realized by combining treatment with a compound or compounds of the compounds of the present invention with one or more additional anti-cancer agents or treatments. The choice of such combinations will depend on various factors including, but not limited to, the type of disease, the age and general health of the subject, the aggressiveness of disease progression, and the ability of the subject to tolerate the agents that comprise the combination.

Thus, a variety of chemical compounds, also described as "anti-neoplastic" agents or "chemotherapeutic agents" can be used in combination with one or more of the novel anti-cancer compounds of the presently described subject matter. Such compounds include, but are not limited to, alkylating agents, DNA intercalators, protein synthesis inhibitors, inhibitors of DNA or RNA synthesis, DNA base analogs, topoisomerase inhibitors, anti-angiogenesis agents, and telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin, also can be combined with compounds of the compounds of the present invention in pharmaceutical compositions. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be combined with the inhibitor compounds of the compounds of the present invention to provide a suitable cancer treatment.

Thus, current chemotherapeutic agents that can be used in a combination treatment with the PFKFB3 inhibitor compounds of the present invention include, but are not limited to, adrimycin, 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chjlorambucil, bisulfan, nitrosurea, dactinomycin, duanorubicin, doxorubicin, bleomycin, plicomycin, tamoxifen, taxol, transplatimun, vinblastin, and methotrexate, and the like.

Combination treatments involving compounds of the present invention can be tested and another therapeutic agent, such as another chemotherapeutic agent can be achieved by using both agents at the same time. Alternatively, treatment with compounds of the present invention can precede or follow treatment with the other agent by intervals ranging from minutes to weeks.

The compounds of the present invention can be tested to measure their ability to inhibit growth of cancer cells, to induce apoptosis of the cancer cells, to reduce tumor burden, and to inhibit metastases. For example, one can measure cell growth according to the MTT assay, the Alamar Blue assay or the cell Titer Glow assay. Growth assays as measured by the methods listed above are well known in the art and measure either directly the number of viable cells (MTT and Alamar Blue assays) or the intracellular levels of ATP, inferring from the viability of cells (Cell Titer glow assay).

Accordingly, in one embodiment, a compound or its tautomeric, enantiomeric or diastereomeric form or a pharmaceutically acceptable salt, prodrug, or metabolite thereof is provided, said compound having the formula:

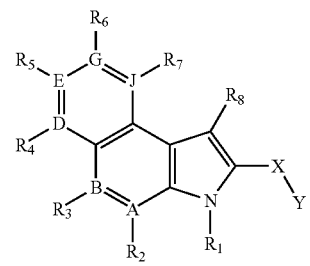

Formula (I)

wherein:

A, B, D, E, G and J are independently selected from the group consisting of N or C substituted with one of $R_2$, $R_3$, $R_4$, $R_5$, $R_6$ or $R_7$, wherein if A, B, D, E, G, or J are N, then $R_2$, $R_3$, $R_4$, $R_5$, $R_6$ or $R_7$ represent a free electron pair at the N atom.

In compounds of Formula I, $R_1$ is selected from the group consisting of hydrogen and linear or branched ($C_1$-$C_6$)-alkyl. In a more specific embodiment, $R_1$ is hydrogen or linear or branched ($C_1$-$C_3$)-alkyl. In a more specific embodiment, $R_1$ is hydrogen or methyl.

In compounds of Formula I, $R_2$, $R_3$, $R_4$, $R_5$, $R_6$ and $R_7$ are independently of one another, when attached to N, a free electron pair; or, when attached to C, are selected from the group consisting of hydrogen, halogen, —COOH, linear or branched ($C_1$-$C_6$)-alkyl, linear or branched ($C_1$-$C_6$)-alkoxy, hydroxyl, —$NH_2$, N ($C_1$-$C_6$)-alkyl, N-di-($C_1$-$C_6$)-alkyl, and —$SO_2CH_3$. In a more specific embodiment, when attached to C, $R_2$, $R_3$, $R_4$, $R_5$, $R_6$ and $R_7$ are selected from the group consisting of hydrogen, halogen, —COOH, linear or branched ($C_1$-$C_3$)-alkyl, linear or branched ($C_1$-$C_3$)-alkoxy, hydroxyl, —$NH_2$, N ($C_1$-$C_3$)-alkyl, N-di-($C_1$-$C_3$)-alkyl, and —$SO_2CH_3$.

In compounds of Formula I, $R_8$ is selected from the group consisting of hydrogen and linear or branched ($C_1$-$C_6$)-alkyl. In a more specific embodiment, $R_8$ is selected from the group consisting of hydrogen and linear or branched ($C_1$-$C_3$)-alkyl.

In compounds of Formula I, X is

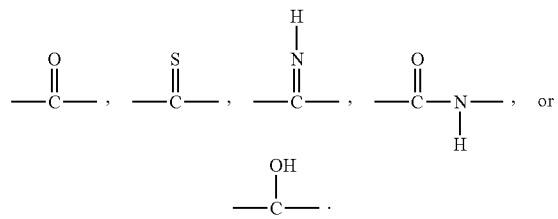

In compounds of Formula I, Y is selected from the group consisting of substituted or unsubstituted ($C_6$-$C_{14}$)-aryl, substituted or unsubstituted heteroaryl comprising from 5 to 13 member atoms and having at least one of N, N=O, NH, N—($C_1$-$C_6$) -alkyl, O, or S as ring members, and substituted or unsubstituted ($C_3$-$C_8$)-cycloalkyl. In a specific embodiment, the ring member is N or NH. In another specific embodiment, when Y is substituted ($C_6$-$C_{14}$)-aryl, substituted heteroaryl comprising from 5 to 13 member atoms, or substituted ($C_3$-$C_8$)-cycloalkyl, substitutents are selected from the group consisting of halogen, linear or branched ($C_1$-$C_6$)-alkyl, linear or branched ($C_1$-$C_6$)-alkoxy, hydroxyl, —OBn, —COOMe, —COOH, —$NH_2$, —$CH_2OH$, N—($C_1$-$C_6$)-alkyl, N-di-($C_1$-$C_6$)-alkyl, and —N—$SO_2CH_3$. In another specific embodiment, when Y is substituted ($C_6$-$C_{14}$)-aryl, substituted heteroaryl comprising from 5 to 13 member atoms, or substituted ($C_3$-$C_8$)-cycloalkyl, substituents are selected from the group consisting of fluorine, chlorine, bromine, iodine, methyl and methoxy.

In another embodiment, a pharmaceutical composition for the treatment of cancer is provided, the composition comprising a compound according to Formula I and at least one pharmaceutically acceptable carrier. In another embodiment, the pharmaceutical composition further comprises one or more additional chemotherapeutic agents.

In another embodiment, a method of treating cancer is provided, the method comprising administering to a subject in need thereof an effective amount of a compound according to Formula I.

In another embodiment, a method of treating a tumor is provided, the method comprising administering to a subject in need thereof an effective amount of a compound according to Formula I.

In still another embodiment, a method of inhibiting glycolytic flux in a cell is provided, the method comprising contacting the cell with an effective amount of a compound according to Formula I.

In another embodiment, a method of inhibiting enzymatic activity of PFKFB3 in a cell is provided, the method comprising contacting the cell with an effective amount of a compound according to Formula I.

EXAMPLES

The following examples are given by way of illustration only and are in no way intended to limit the scope of the present invention.

Example 1

Inhibition of Cancer Cell Proliferation

The ability of the compounds described herein to kill or inhibit the proliferation of cancer cells was measured using either the MTT assay, or the Alamar Blue assay, or the Cell Titer Glow® assay using 48 or 72 hours exposure. Results for different cancer cell lines are shown in the Tables 2, 3, and 4 below and demonstrate that these compounds inhibit cancer cell proliferation at low nanomolar concentrations across many types of cancer cell lines. The procedures are briefly described below. Cells of the desired tumor cell line were plated at $2 \times 10^5$ cells/ml in 96 well plates. Twice the indicated concentrations of the compounds of the invention were added to cells the following day in an equal volume of media. 72 hours later, cells were lysed and subjected to ATP determination using the CellTiter Glo-Luminescent Cell Viability Assay kit (Promega, Madison, Wis.). Experiments were done in triplicate. When using the MTT assay or the Alamar blue assay, the experimental conditions are essentially similar; at the end of the incubation period, 20 microliters of the MTT solution is added per well and the samples are incubated for an additional four hours, rinsed, and the absorbance at 570 nm measured. Results for the inhibition of cells proliferation are reported as $IC_{50}$ values as commonly done (the concentration leading to a 50% inhibition of proliferation of the cell population) and are listed in the Tables below. Table 2 lists the $IC_{50}$ values for the compounds of the invention in several cell lines including Jurkat, Calu-6, NCI-H82, U937, HCT-116, and MDA-MB-231 cancer cell lines. Table 3 lists the $IC_{50}$ of PFK-095 in a panel of 13 cell lines and Table 4 lists values for PFK-112 in a different panel of 10 cell lines.

TABLE 2

$IC_{50}$ values (Alamar Blue assay, 72 hours)

| | Jurkat | STD | Calu-6 | STD | NCI-H82 | STD | U937 | STD | HCT-116 | STD | MDA-MB-231 | STD |
|---|---|---|---|---|---|---|---|---|---|---|---|---|
| ACT-PFK-065 | 0.775 | 0.386 | 0.267 | 0.211 | 0.283 | 0.057 | 0.165 | 0.298 | 1.313 | 0.792 | 0.625 | 0.247 |
| ACT-PFK-095 | 1.500 | 0.566 | 0.208 | 0.035 | 0.498 | 23.087 | 0.050 | 0.007 | 2.400 | 0.141 | 0.395 | 0.120 |
| ACT-PFK-095HCl | 0.440 | 0.014 | 0.390 | 0.064 | 0.305 | 0.035 | 0.020 | 0.000 | 0.850 | 0.212 | — | |
| ACT-PFK-096 | 1.500 | 0.141 | 0.020 | 0.014 | 0.155 | 0.049 | 0.014 | 0.003 | 0.695 | 0.120 | — | |
| ACT-PFK-098 | 0.405 | 0.106 | 0.220 | 0.014 | 0.210 | 0.000 | 0.040 | 0.000 | 0.490 | 0.127 | — | |
| ACT-PFK-099 | 0.410 | 0.014 | 0.230 | 0.014 | 0.680 | 0.014 | 0.076 | 0.008 | 0.495 | 0.064 | — | |
| ACT-PFK-101 | >100 | — | >100 | — | >100 | — | >100 | — | — | — | — | |
| ACT-PFK-102 | >100 | — | >100 | — | >100 | — | >100 | — | — | — | — | |
| ACT-PFK-103 | 0.110 | 0.071 | 0.130 | 0.028 | 0.405 | 0.049 | — | | 0.360 | 0.071 | 6.400 | 1.838 |
| ACT-PFK-104 | 0.118 | 0.032 | 0.200 | 0.014 | 0.310 | 0.028 | — | | 0.320 | 0.014 | 5.950 | 0.283 |
| ACT-PFK-105 | 0.115 | 0.049 | 0.140 | 0.000 | 0.395 | 0.007 | 0.070 | 0.000 | 0.355 | 0.021 | 7.400 | 1.131 |

TABLE 2-continued

IC$_{50}$ values (Alamar Blue assay, 72 hours)

| | Jurkat | STD | Calu-6 | STD | NCI-H82 | STD | U937 | STD | HCT-116 | STD | MDA-MB-231 | STD |
|---|---|---|---|---|---|---|---|---|---|---|---|---|
| ACT-PFK-106 | 21.000 | 5.657 | 8.900 | 1.131 | 15.000 | 2.828 | 3.150 | 0.071 | 38.500 | 0.707 | 28.000 | 14.142 |
| ACT-PFK-107 | 6.900 | 0.424 | 7.250 | 0.354 | 10.100 | 6.223 | 2.850 | 0.212 | >100 | — | 11.650 | 0.354 |
| ACT-PFK-108 | 0.545 | 0.087 | 0.360 | 0.113 | 0.360 | 0.057 | 0.205 | 0.010 | 0.475 | 0.096 | 0.090 | 0.000 |
| ACT-PFK-109 | >100 | — | 64.500 | 0.707 | >100 | — | >100 | — | >100 | — | >100 | — |
| ACT-PFK-110 | >100 | — | 59.500 | 0.014 | >100 | — | >100 | — | >100 | — | >100 | — |
| ACT-PFK-111 | >100 | 0.141 | 57.500 | 17.678 | 40.200 | 0.283 | 57.250 | 6.010 | 63.500 | 10.607 | >100 | — |
| ACT-PFK-112 | 0.625 | 0.320 | 0.260 | 0.139 | 0.685 | 0.096 | 0.130 | 0.008 | 1.443 | 0.590 | 0.205 | 0.021 |
| ACT-PFK-113 | 28.000 | 1.414 | 28.500 | 16.263 | >100 | — | 26.800 | 1.697 | >100 | — | >100 | 0.120 |
| ACT-PFK-114 | >100 | — | >100 | — | >100 | — | >100 | — | >100 | — | >100 | — |
| ACT-PFK-115 | 4.550 | 1.644 | 2.175 | 0.727 | 6.050 | 1.926 | 1.073 | 0.098 | 8.200 | 3.732 | 0.620 | 0.240 |
| ACT-PFK-116 | 0.125 | 0.021 | 0.080 | 0.028 | 0.205 | 0.021 | 0.030 | 0.014 | 0.235 | 0.007 | 0.563 | 0.120 |
| ACT-PFK-118 | 0.240 | 0.057 | 0.420 | 0.028 | 0.385 | 0.021 | 0.095 | 0.007 | 1.700 | 0.424 | 0.673 | 0.163 |
| ACT-PFK-119 | 0.110 | 0.014 | 0.070 | 0.014 | 0.315 | 0.007 | 0.070 | 0.028 | 0.365 | 0.007 | 0.620 | 0.240 |
| ACT-PFK-120 | 0.155 | 0.007 | 0.055 | 0.007 | 0.270 | 0.021 | — | | — | | — | |
| ACT-PFK-121 | 0.115 | 0.021 | 0.079 | 0.013 | 0.335 | 0.014 | — | | — | | — | |
| ACT-PFK-122 | 0.235 | 0.014 | 0.070 | 0.014 | 0.320 | 0.028 | — | | — | | — | |
| ACT-PFK-123 | 0.100 | 0.014 | 0.079 | 0.013 | 0.315 | 0.007 | — | | — | | — | |
| ACT-PFK-124 | 8.800 | 1.131 | 10.350 | 3.748 | 11.150 | 3.394 | — | | — | | — | |
| ACT-PFK-125 | 22.700 | 0.990 | 39.500 | 1.131 | 20.300 | 1.131 | — | | — | | — | |
| ACT-PFK-126 | 0.850 | 0.071 | 1.100 | 0.141 | 0.840 | 0.057 | — | | — | | — | |
| ACT-PFK-127 | 0.780 | 0.106 | 1.020 | 0.042 | 0.755 | 0.078 | — | | — | | — | |
| ACT-PFK-128 | >100 | — | >100 | — | >100 | — | — | | — | | — | |
| ACT-PFK-129 | 0.230 | 0.057 | 0.355 | 0.028 | 0.370 | 0.007 | — | | — | | — | |
| ACT-PFK-130 | 1.130 | 0.262 | 1.650 | 0.071 | 1.450 | 0.354 | — | | — | | — | |
| ACT-PFK-131 | >100 | — | >100 | — | >100 | — | — | | — | | — | |

TABLE 2-continued

IC$_{50}$ values (Alamar Blue assay, 72 hours)

| | Jurkat | STD | Calu-6 | STD | NCI-H82 | STD | U937 | STD | HCT-116 | STD | MDA-MB-231 | STD |
|---|---|---|---|---|---|---|---|---|---|---|---|---|
| ACT-PFK-132 | 10.100 | 0.141 | 10.650 | 0.212 | 9.650 | 0.071 | — | | — | | — | |
| ACT-PFK-133 | 2.350 | 0.778 | 40.850 | 0.212 | 11.900 | 1.414 | — | | — | | — | |
| ACT-PFK-134 | 3.300 | 1.131 | 2.450 | 0.212 | 3.450 | 0.636 | — | | — | | — | |

TABLE 3

IC$_{50}$ values (MTT assay, 72 hours) in a panel of cell lines using PFK-095

| Cell line | PFK-095 IC$_{50}$ (microM) |
|---|---|
| K562 | 0.21 |
| MDA-MB-231 | 24.9 |
| Jurkat | 4.65 |
| H209 | 0.19 |
| Hela | 9.1 |
| HT-29 | 0.45 |
| HCT-116 | 0.51 |
| U937 | 0.05 |
| NCI-H82 | 0.18 |
| Calu-6 | 0.14 |
| Hep G2 | 5.5 |
| DU145 | 0.94 |
| PC3 | 0.95 |

TABLE 4

IC$_{50}$ values (MTT assay, 48 hours) in a panel of cell lines using PFK-112

| Cell line | PFK-112 IC$_{50}$ (nM) |
|---|---|
| H22 | 513 |
| CT26 | 1954 |
| U87MG | 3786 |
| SK-N-SH | 305 |
| LnCap | 1030 |
| A549 | 822 |
| MiaPaca | 154 |
| BX-PC-3 | 135 |
| BT474 | 1370 |
| SK-BR-3 | 1112 |

Example 2 Inhibition of PFKFB3, the Recombinant Protein

The inducible bifunctional 6-Phosphofructo-2-kinase/fructose 2,6-biphosphatase 3 enzyme (PFKFB3) was expressed and purified in order to determine if the compounds of the invention inhibit its enzymatic activity. PFKFB3 was prepared by expression in *E. coli* and purified by GST column and column chromatography. SDS Page coumassie staining gels indicated that purity was high (>95%). The recombinant protein was pure and active as determined by the results of a kinase activity assay commercially available (such as ADP Glow® assay, InVitrogen). The same assay was used to determine the inhibition of the protein and the results are shown in Table 5 below (IC$_{50}$ values or percent inhibition at a fixed concentration). Results confirmed that the compounds of the invention have low nanomolar IC$_{50}$ values, interacting with PFKFB3 and inhibiting its enzymatic activity.

TABLE 5

PFKFB3 Inhibition results at a fixed compound concentration (250 nM).

% Inhibition of PFKFB3 Enzymatic Activity, 250 nM analog concentration

| | PFK065 | PFK095 | PFK096 | PFK100 | PFK111 | PFK112 | PFK116 | PFK118 | PFK119 | PFK123 |
|---|---|---|---|---|---|---|---|---|---|---|
| % Inhib. | 13.5 | 26.2 | 0 | 0 | 54.3 | 81.5 | 34.2 | 0 | 3.7 | 19.4 |

Example 3

Microsomal Stability in Human Liver Microsomes

Microsomal stability in vitro in different biologic media (liver microsomes, S9 fraction, hepatocytes) and species is ascertained to evaluate the rate at which a compound undergoes metabolism in the experimental in vitro conditions. Results for some compounds of the invention after a 60 minutes incubation period in human liver microsomes are shown in the Table 6 below. Results show that the rate of metabolism in vitro can be controlled as substitutions lead to metabolism rates varying between 20% and 100%. Experimental conditions are briefly described here: the stability in human liver microsomes of several compounds was done over 24 hours at 37° C. using pooled mixed gender human liver microsomes.

These liver microsomes were prepared at 1.0 mg/ml of microsomal protein in a 100 mM potassium phosphate pH 7.4 buffer with 1 mM NADPH. The media was incubated at 37° C. with the compound in solution in DMSO. The concentration of the compound was followed by LC/MS-MS as a function of time. Samples were assayed at t=0, 15, 30, and 60 minutes. Testosterone was used as a positive control. The same experiment was performed with mouse, rat or dog liver microsomes instead of human liver microsomes.

TABLE 6

Human Liver Microsomal stability results.

| Compound | HLM, Mean metabolized (%) | |
|---|---|---|
| | 0 min | 60 min |
| ACT-PFK-065 | 0.0 | 93 |
| ACT-PFK-093 | 0.0 | 95 |
| ACT-PFK-095 | 0.0 | 26 |
| ACT-PFK-096 | 0.0 | 99 |
| ACT-PFK-104 | 0.0 | 80 |
| ACT-PFK-105 | 0.0 | 51.4 |
| ACT-PFK-107 | 0.0 | 100.0 |
| ACT-PFK-108 | 0.0 | 73.3 |
| ACT-PFK-112 | 0.0 | 82.7 |
| ACT-PFK-115 | 0.0 | 99.6 |
| ACT-PFK-116 | 0.0 | 45.8 |
| ACT-PFK-118 | 0.0 | 22.2 |
| ACT-PFK-119 | 0.0 | 79.2 |

Example 4

Cell Permeability

The determination of the permeability in Caco2 or MDR1-MDCK cells is widely used when screening compounds to assess cell permeability, intestinal drug transport and predict absorption rates and to ascertain if a compound might be a Pgp substrate and have cross the blood brain barrier. High permeability is determined as $P_{app} > 10 \times 10^{-6}$ cm/s and suggests that a compound might be orally absorbed. Comparison of the apical to basal (A-B) and basal to apical (B-A) values show if a compound is actively effluxed out the cells and if it is a Pgp substrate. Results for several compounds are shown below and suggest that the compounds of the invention have high permeability properties, are not Pgp substrates, may be orally bioavailable and may cross the blood brain barrier. Briefly, cell permeability and transport mechanisms in Caco-2 and MDR1-MDCK monolayers experiments were performed in triplicate in the apical-to-basolateral and basolateral-to-apical direction using Transwell wells containing either Caco-2 or MDR1-MDCK monolayers. A modified Hanks buffer pH 7.4 was used in both reservoir and receiver wells with the addition of 1% BSA in the receiver side. Confluent monolayers were used and their integrity was verified using reference compounds (Atenolol as a low permeability reference compound and Propanolol as a high permeability reference compound). A sample in the basolateral and apical sides was taken after 2 hours and the concentration measured by LC/MS-MS. Results are summarized in Tables 7A and 7B below. The results also suggested that these compounds are not P-gp substrates and that they may cross the blood brain barrier.

TABLE 7A

Permeability values in Caco2 cells

| | $P_{app}$ (cm/sec $10^{-6}$) | |
|---|---|---|
| Compounds | (A-B) | (B-A) |
| ACT-PFK-065 | 10.3 | 5.9 |
| ACT-PFK-095 | 16.2 | 8.9 |

TABLE 7B

Permeability values in MDR1-MDCK cells

| | $P_{app}$ (cm/sec $10^{-6}$) | |
|---|---|---|
| Compounds | (A-B) | (B-A) |
| ACT-PFK-112 | 7.8 | 17.3 |

Example 5

Solubility Measurements

Chemical properties of the compounds of the invention were investigated, including the solubility in several solvents and pharmaceutically accepted excipients. Results show the solubility profile can be modified, resulting in solubility values in the mg/ml range that are satisfactory in order to treat cancer patients. Briefly, selected compounds of the invention are dissolved in a small volume of the solvents/excipients of interest at room temperature over 1 hour in typically 1 ml and the concentration is measured by HPLC after filtration.

TABLE 8

Solubility results after 1 hour at room temperature

| Cpd | EtOH | Acetone | DCM | Cremophor | Tween 80 | Cre:EtOH[1] | Twee80:EtOH[2] | Cre:EtOH:Saline[3] |
|---|---|---|---|---|---|---|---|---|
| PFK-095 | 1.6 | 5.0 | 3.4 | 6.9 | 7.4 | 10 | 9.7 | 0.3 |
| PFK-096 | 2.8 | 25.8 | 8.9 | 1.2 | 1.8 | 29.7 | 18.7 | 1.7 |
| PFK-098 | 4.6 | 9.3 | 10.4 | 30.2 | 37 | 29 | 32.8 | 2.4 |
| PFK-108 | 9.9 | 12.8 | 11.1 | 37.6 | 16.9 | 78.1 | 10.3 | 4.8 |
| PFK-112 | 7.4 | 8.2 | 14 | 18.6 | 18.1 | 37.6 | 35.6 | 3.7 |
| PFK-116 | 1.3 | 6.2 | 6 | 14.4 | 15.5 | 8.6 | 10.2 | 0.7 |
| PFK-118 | 0.2 | 0.6 | 0.3 | 2.2 | 1.6 | 1 | 1.3 | 0.1 |
| PFK-119 | 1 | 5.5 | 0.7 | 14.4 | 11.4 | 6.1 | 8.6 | 0.3 |

[1]Cre:EtOH is a 1:1 cremophor EL-P:ethanol mixture
[2]Tween80:EtOH is a 6:4 mixture
[3]Cre:EtOH:Saline is a 5:5:90 mixture

Example 6

Inhibition of 2-Deoxyglucose Uptake

Inhibition of PFKFB3 results in inhibiting glycolysis. Several feedback or feedforward activation and inhibition mechanisms exist so that, by a feedback mechanism, inhibiting the activity of PFKFB3 may inhibit glucose uptake by cells. An assay was developed to determine if there was inhibition of glucose uptake following exposure to the compounds on the invention. Briefly, Jurkat cells were plated at $1 \times 10^5$/mL in RPM' 1640 supplemented with 10% fetal bovine serum and 50 µg/mL gentamicin sulfate. Cells were immediately treated with vehicle or 5 µmol/L of the compound of the invention for 3 hours and subsequently placed in glucose-free RPMI 1640 for 30 min. $^{14}$C-2-deoxyglucose (0.25 µCi/mL; Perkin Elmer) was added for an additional 60 min and cells were then washed three with ice-cold RPMI 1640 containing no glucose. Cell lysates were collected in 500 µL of 0.1% SDS, and scintillation counts (counts/min) were measured on 400 µL of lysate. Counts were normalized to protein concentration.

Results shown in Table 9 indicate a rapid and quantitative inhibition of glucose uptake by cells treated with PFKFB3 inhibitors.

TABLE 9

Percentage of Deoxyglucose Uptake Inhibition.

| Compound | Concentration | % Inhibition in 2-Deoxyglucose Uptake |
| --- | --- | --- |
| PFK-095 | 5 µM | 48 |
| PFK-096 | 5 µM | 29 |
| PFK-098 | 5 µM | 25 |
| PFK-108 | 5 µM | 2 |
| PFK-109 | 5 µM | 42 |
| PFK-112 | 5 µM | 47 |
| PFK-116 | 5 µM | 0 |

Example 7

Pharmacokinetics

The pharmacokinetic parameters for several compounds were determined in mice following IV (intravenous), IP (intraperitoneal), or PO (per os) administration, as well as in rats and dogs. A typical study design includes six Balbc male mice 7 to 8 weeks old. For instance, a dose of 10 mg/kg was administered IV using a 5% DMSO/90% Captisol (20% in water) solution or other pharmaceutically acceptable parenteral and oral formulations. Blood samples were collected at different intervals. Plasma samples were extracted and analyzed using an LC-MS/MS method. Similar protocols were used for the rats (Sprague Dawley rats) or dogs (beagles) PK studies; in the case of dogs PK studies, the number of animals per group was three.

Figure 2:
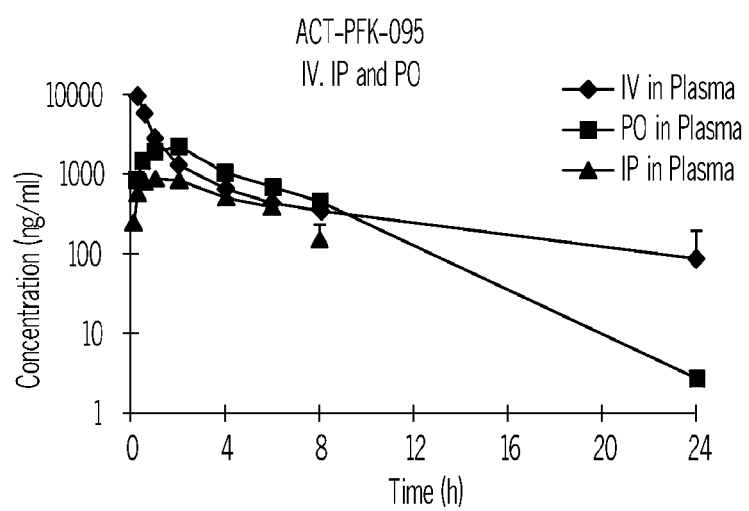
Figure 3:
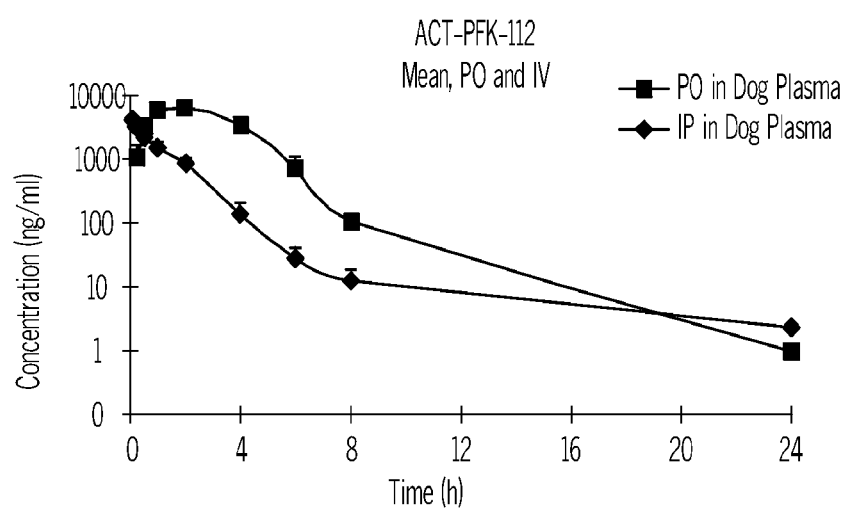
FIG. 3 shows the time vs. plasma concentration pharmacokinetic profile of ACT-PFK-112 in male beagle dogs (IV dosing: 6 mg/kg; PO dosing, 24 mg/kg).

Results illustrated in FIGS. 1 to 3 show that the compounds of the invention have good pharmacokinetic properties and that they are orally bioavailable with F (the oral bioavailability) varying between 25% for PFK-065 and 95% for PFK-112.

Table 10 shows the IV pharmacokinetic parameters for compounds dosed intravenously. PFK-065 was dosed at 10 mg/kg in male Balbc mice; PFK-095 was dosed at 10 mg/kg in male Sprague Dawley rats; and PFK-112 dosed at 6 mg/kg in male beagle dogs.

TABLE 10

IV PK parameters for PFK-065, PFK-095, and PFK-112

| | $T_{1/2b}$ (h) | $C_{max}$ (ng/mL) | $AUC_{0\text{-}inf}$ (ng · h/ml) | Vd (L/kg) | % F (from PO group) |
| --- | --- | --- | --- | --- | --- |
| PFK-065 | 2.1 | 4112 | 2627 | 11.2 | 25% |
| PFK-095 | 5.5 | 16932 | 1293 | 2.5 | 38% |
| PFK-112 | 5.8 | 5065 | 5066 | 1.8 | 95% |

Example 9

Efficacy Studies

The activity of several compounds of the invention was investigated in vivo in tumor models. Several tumor models were used in these studies (the Lewis Lung carcinoma model, the human glioblastoma xenograft U87MG tumor model, the human colorectal carcinoma cancer model HCT-116, the CT-26 colon carcinoma cancer model, the Lung Calu-6 model, the BT474 breast carcinoma model). The experimental protocol for the U87MG study is described below. Subsequent to subcutaneous inoculation of tumor cells, tumors started to develop and once tumors reached the desired volume of 150 mm$^3$ on average, treatment was initiated. Tumor volume was monitored in both groups and the average for both the control and treatment groups three times a week, as well as body weights.

Briefly, athymic nude mice at 7-8 weeks of age were used for the study. Mice were housed in microisolator housing, with food and water provided as libitum, and quarantined for 4 days prior to the initiation of the study. U87MG cells were maintained in McCoy's 5A medium supplemented with 10% fetal bovine serum and 2 mM glutamine. Cells at 80% confluence were harvested using 0.25% trypsin/EDTA solution, washed once with PBS and resuspended in a mixture of serum-free medium/Matrigel (1:1 by volume) at a density of 3×10 6 cells/100 µl. 4 groups of 10 mice each were used in that experiment. U87MG cells suspended in 100 µl of a mixture of medium/Matrigel (1:1) were subcutaneously implanted in the right flank region. Animals were monitored for tumor growth daily after cell implantation. When tumor volumes reached approximately 150 mm3, mice were randomized into 2 groups of 8 mice each using only mice having tumor volumes closest to the mean value. Tumor volumes were measured using the formula V=L×W×H×π/6, where L and W represent the longer and shorter diameters of the tumor and H represents the height of the tumor. Treatment began following randomization. ACT-PFK-112 was administered IV at a dose of 50 mg/kg on days 1, 2, 3, 7, 8, 9, 13, 14, and 15. Animals were observed for possible toxic effect from the drug treatment. Body weights were recorded and showed that the compounds were very well tolerated.

Similar protocols were used for the other studies using different models;

differences include the use of normal mice (C57Bl/6); administering larger number of cancer cells; including a positive control group; dosing using different routes of administration and different schedules or doses.

Figure 4:
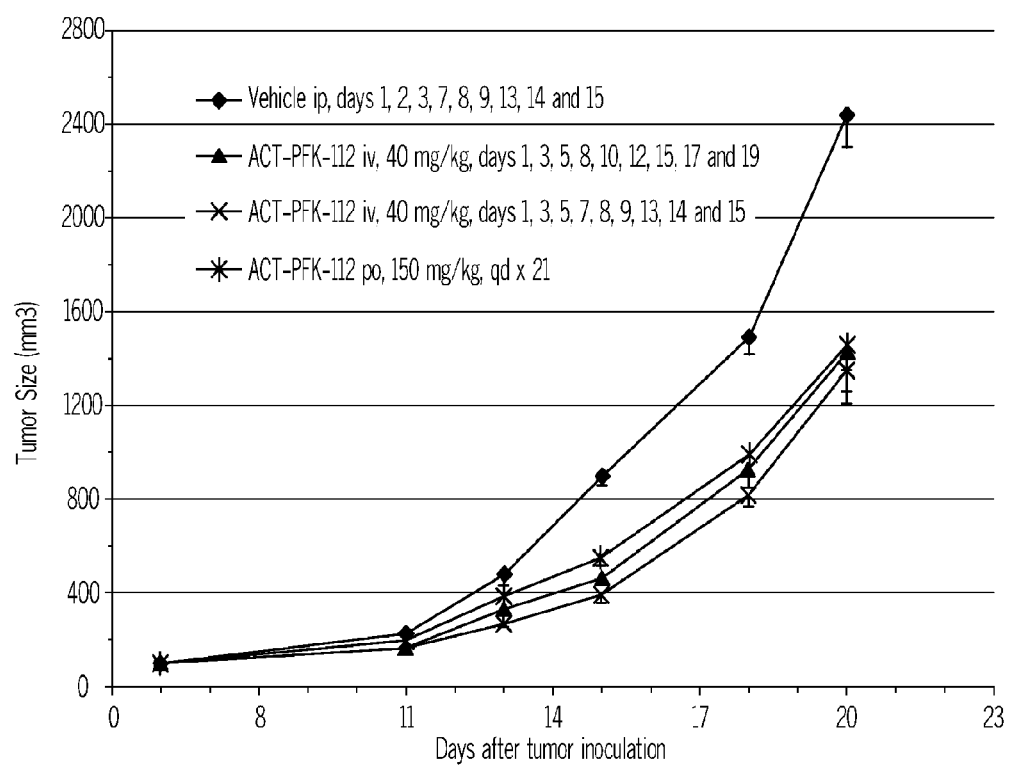
FIG. 4 shows the average tumor volume as a function of time for control group and treatment groups in the Lewis Lung Carcinoma (ACT-PFK-112 dosed IV at 50 mg/kg using 2 different schedules that are listed on the graph and dosed PO daily at 150 mg/kg).
Figure 5:
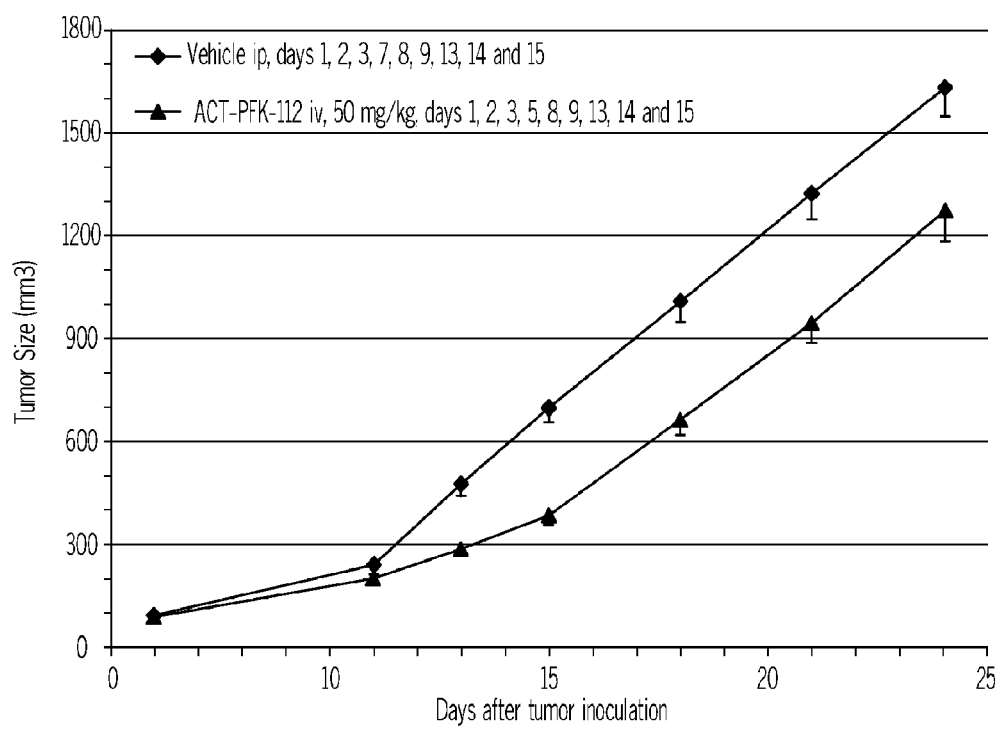
FIG. 5 shows the average tumor volume as a function of time for control group and treatment group in the CT-26 colon carcinoma model (ACT-PFK-112 dosed IV at 40 mg/kg using the schedule specified on the graph).
Figure 6:
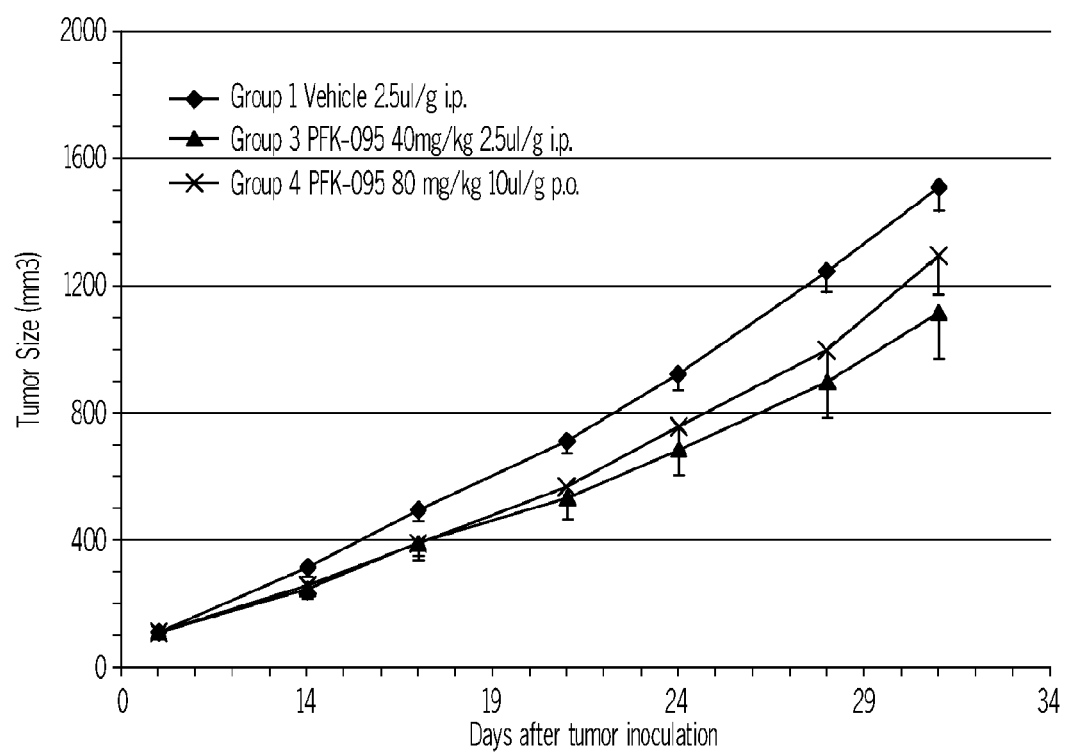
FIG. 6 shows the average tumor volume as a function of time for control group and treatment group in the HCT-116 tumor model (ACT-PFK-095 dosed IP at 40 mg/kg and PO at 80 mg/kg).

Results of several studies are shown in FIGS. 4 to 6 and demonstrate that compounds of the invention effectively inhibit tumor growth in vivo in different tumor types.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:

1. A compound or its tautomeric, enantiomeric or diastereomeric form or a pharmaceutically acceptable salt, said compound having the formula:

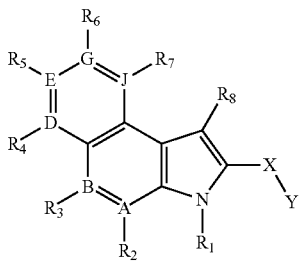

Formula (I)

wherein:
A, B, D, E, G and J are independently selected from the group consisting of N or C substituted with one of $R_2$, $R_3$, $R_4$, $R_5$, $R_6$ or $R_7$, wherein if A, B, D, E, G, or J are N, then $R_2$, $R_3$, $R_4$, $R_5$, $R_6$ or $R_7$ represent a free electron pair at the N atom;
$R_1$ is selected from the group consisting of hydrogen and methyl;
$R_2$, $R_3$, $R_4$, $R_5$, $R_6$ and $R_7$ are independently of one another, when attached to N, a free electron pair, or, when attached to C, are selected from the group consisting of hydrogen, halogen, methyl, methoxy, hydroxyl, —$NH_2$, and —$SO_2CH_3$;
$R_8$ is selected from the group consisting of hydrogen and ($C_1$-$C_6$)-alkyl;

X is 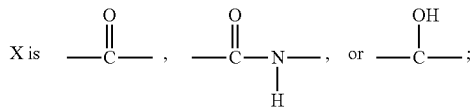

and
Y is selected from the group consisting of substituted or unsubstituted $C_6$ aryl, and substituted or unsubstituted heteroaryl comprising 6 member atoms and having at least one of N, N=O, NH, or N-($C_1$-$C_6$)-alkyl as ring members, wherein when Y is substituted aryl or substituted heteroaryl, substituents are selected from the group consisting of halogen, ($C_1$-$C_6$)-alkyl, ($C_1$-$C_6$)-alkoxy, hydroxyl, —OBn, —COOMe, —COOH, —$NH_2$, —$CH_2OH$, N-di-($C_1$-$C_6$)-alkyl, and —N—$SO_2CH_3$, with the proviso that where A, B, D, E, G and J are each carbon, and $R_1$, $R_2$, $R_3$, $R_4$, $R_5$, $R_6$, $R_7$ and $R_8$ are each hydrogen, if X is

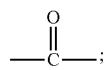

and Y is $C_6$-aryl, then Y is substituted, and if X is

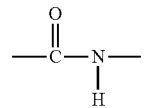

and Y is a substituted $C_6$-aryl, then a substituent may not be —$NH_2$.

2. The compound of claim 1, wherein when Y is substituted aryl, or substituted heteroaryl, wherein substituents are selected from the group consisting of fluorine, chlorine, bromine, iodine, methyl, and methoxy.

3. A pharmaceutical composition for the treatment of cancer comprising a compound according to claim 1 and at least one pharmaceutically acceptable carrier.

4. The pharmaceutical composition of claim 3, further comprising one or more additional chemotherapeutic agents.

5. A compound selected from the group consisting of: (3H-Benzo[e]indol-2-yl)-(4-methoxy-phenyl)-methanone; (3H-Benzo[e]indol-2-yl)-pyridin-4-yl-methanone; (3H-Benzo[e]indol-2-yl)-pyridin-4-yl-methanone.HC1; (3H-Benzo[e]indol-2-yl)-(3-methoxy-phenyl)-methanone; (3H-Benzo[e]indol-2-yl)-pyridin-3-yl-methanone; (3H-Benzo[e]indol-2-yl)-(2-hydroxy-phenyl)-methanone; (3H-Benzo[e]indol-2-yl)-(4-hydroxy-phenyl)-methanone; (5-Methyl-3H-benzo[e]indol-2-yl)-phenyl-methanone; Phenyl-(7H-pyrrolo[2,3-h]quinolin-8-yl)-methanone; 3H-Benzo[e]indol-2-yl)-(3-hydroxy-phenyl)-methanone; (5-Fluoro-3H-benzo[e]indol-2-yl)-phenyl-methanone; (3H-benzo[e]indol-2-yl)-(1-oxy-pyridin-4-yl)-methanone; (3H-Benzo[e]indol-2-yl)-(4-benzyloxy-3-methoxy-phenyl)-methanone; 4-(3H-Benzo[e]indole-2-carbonyl)-benzoic acid methyl ester; 5-(3H-Benzo[e]indole-2-carbonyl)-2-benzyloxy-benzoic acid methyl ester; 5-(3H-Benzo[e]indole-2-carbonyl)-2-benzyloxy-benzoic acidmethanone; (5-Fluoro-3H-benzo[e]indol-2-yl)-pyridin-4-yl-methanone; (4-Benzyloxy-3-methoxy-phenyl)-(5-fluoro-3H-benzo[e]indo -2-yl)-methanone; (3H-Benzo[e]indol-2-yl)-(3-methoxy-phenyl)-methanol; (3H-Benzo[e]indol-2-yl)-pyridin-4-yl-methanol; 3H-Benzo[e]indole-2-carboxylic acid phenylamide; 3H-Benzo[e]indole-2-carboxylic acid (3-methoxy-phenyl)-amide; and (3H-Benzo[e]indol-2-yl)-(4-dimethylamino-phenyl)-methanone.

6. A compound selected from the group consisting of:
(3H-Benzo[e]indol-2-yl)-(2-methoxy-phenyl)-methanone;
(3H-benzo[e]indol-2-yl)-(2-chloro-pyridin-4-yl)-methanone;
(3H-Benzo[e]indol-2-yl)-(4-hydroxy-3-methoxy-phenyl)-methanone;
(4-Amino-phenyl)-(3H-benzo[e]indol-2-yl)-methanone;
(3H-Benzo[e]indol-2-yl)-(2-methoxy-pyridin-4-yl)-methanone;
(5-Fluoro-3H-benzo[e]indol-2-yl)-(3-methoxy-phenyl)-methanone;
(5-Fluoro-3H-benzo[e]indol-2-yl)-(4-hydroxy-3-methoxy-phenyl)-methanone;
(3H-Benzo[e]indol-2-yl)-(3-hydroxymethyl-phenyl)-methanone;
(5-Fluoro-3H-benzo[e]indol-2-yl)-(3-fluoro-4-hydroxy-phenyl)-methanone;
(3H-Benzo[e]indol-2-yl)-p-tolyl-methanone;
(4-Amino-3-methoxy-phenyl)-(3H-benzo[e]indol-2-yl)-methanone;

(4-Amino-3-methoxy-phenyl)-(5-hydroxy-3H-benzo[e]indol-2-yl)-methanone;
(4-Amino-3-methoxy-phenyl)-(5-methoxy-3H-benzo[e]indol-2-yl)-methanone;
N-[4-(3H-Benzo[e]indole-2-carbonyl)-phenyl]-methanesulfonamide;
(4-Amino-phenyl)-(5-methoxy-3H-benzo[e]indol-2-yl)-methanone;
(4-Amino-2-fluoro-phenyl)-(5-methoxy-3H-benzo[e]indol-2-yl)-methanone;
(4-Amino-3-fluoro-phenyl)-(5-methoxy-3H-benzo[e]indol-2-yl)-methanone;
(4-Amino-2-methoxy-phenyl)-(5-methoxy-3H-benzo[e]indol-2-yl)-methanone;
(4-Amino-phenyl)-(9-methoxy-3H-benzo[e]indol-2-yl)-methanone;
(4-Amino-3-methoxy-phenyl)-(9-methoxy-3H-benzo[e]indol-2-yl)-methanone;
(4-Amino-2-methoxy-phenyl)-(9-methoxy-3H-benzo[e]indol-2-yl)-methanone;
(4-Amino-3-fluoro-phenyl)-(9-methoxy-3H-benzo[e]indol-2-yl)-methanone;
(4-Amino-2-fluoro-phenyl)-(9-methoxy-3H-benzo[e]indol-2-yl)-methanone;
(4-Amino-3-fluoro-phenyl)-(3H-benzo[e]indol-2-yl)-methanone;
(4-Amino-2-fluoro-phenyl)-(3H-benzo[e]indol-2-yl)-methanone;
(4-Amino-phenyl)-(7-methoxy-3H-benzo[e]indol-2-yl)-methanone;
(4-Amino-phenyl)-(5-hydroxy-3-methyl-3H-benzo[e]indol-2-yl)-methanone;
(7-Amino-5-fluoro-9-hydroxy-3H-benzo[e]indol-2-yl)-(3-methyl-pyridin-4-yl)-methanone;
(5-Amino-3H-pyrrolo[3,2-f]isoquinolin-2-yl)-(3-methoxy-pyridin-4-yl)-methanone;
(4-Amino-2-methyl-phenyl)-(9-hydroxy-3H-pyrrolo[2,3-c]quinolin-2-yl)-methanone; and
(4-Amino-phenyl)-(7-methanesulfonyl-3H-benzo[e]indol-2-yl)-methanone.

7. A compound according to claim 6, selected from the group consisting of:
(3H-Benzo [e]indol-2-yl)-(2-methoxy-phenyl)-methanone;
(3H-benzo [e]indol-2-yl)-(2-chloro-pyridin-4-yl)-methanone;
(3H-Benzo [e]indol-2-yl)-(4-hydroxy-3-methoxy-phenyl)-methanone;
(3H-Benzo [e]indol-2-yl)-(2-methoxy-pyridin-4-yl)-methanone;
(3H-Benzo [e]indol-2-yl)-(3-hydroxymethyl-phenyl)-methanone; and
(3H-Benzo [e]indol-2-yl)-p-tolyl-methanone.

8. A compound according to claim 6, selected from the group consisting of:
(5-Fluoro-3H-benzo [e]indol-2-yl)-(3-methoxy-phenyl)-methanone;
(5-Fluoro-3H-benzo [e]indol-2-yl)-(4-hydroxy-3-methoxy-phenyl)-methanone; and
(5-Fluoro-3H-benzo [e]indol-2-yl)-(3-fluoro-4-hydroxy-phenyl)-methanone.

9. A compound according to claim 6, selected from the group consisting of:
(4-Amino-3-methoxy-phenyl)-(3H-benzo[e]indol-2-yl)-methanone;
(4-Amino-3-methoxy-phenyl)-(5-hydroxy-3H-benzo[e]indol-2-yl)-methanone;
(4-Amino-3-methoxy-phenyl)-(5-methoxy-3H-benzo[e]indol-2-yl)-methanone;
(4-Amino-2-methoxy-phenyl)-(5-methoxy-3H-benzo[e]indol-2-yl)-methanone;
(4-Amino-3-methoxy-phenyl)-(9-methoxy-3H-benzo[e]indol-2-yl)-methanone; and
(4-Amino-2-methoxy-phenyl)-(9-methoxy-3H-benzo[e]indo 2-yl)-methanone.

10. A compound according to claim 6, selected from the group consisting of:
(4-Amino-2-fluoro-phenyl)-(5-methoxy-3H-benzo [e]indol-2-yl)-methanone;
(4-Amino-3-fluoro-phenyl)-(5-methoxy-3H-benzo [e]indol-2-yl)-methanone;
(4-Amino-3-fluoro-phenyl)-(9-methoxy-3H-benzo [e]indol-2-yl)-methanone;
(4-Amino-2-fluoro-phenyl)-(9-methoxy-3H-benzo [e]indol-2-yl)-methanone;
(4-Amino-3-fluoro-phenyl)-(3H-benzo [e]indol-2-yl)-methanone; and
(4-Amino-2-fluoro-phenyl)-(3H-benzo [e]indol-2-yl)-methanone.

11. A compound according to claim 6, selected from the group consisting of:
(4-Amino-phenyl)-(5-methoxy-3H-benzo[e]indol-2-yl)-methanone;
(4-Amino-phenyl)-(9-methoxy-3H-benzo[e]indol-2-yl)-methanone;
(4-Amino-phenyl)-(7-methoxy-3H-benzo[e]indol-2-yl)-methanone;
(4-Amino-phenyl)-(5-hydroxy-3-methyl-3H-benzo[e]indol-2-yl)-methanone;
(4-Amino-phenyl)-(7-methanesulfonyl-3H-benzo[e]indol-2-yl)-methanone.

12. A compound according to claim 6, selected from the group consisting of:
N-[4-(3H-Benzo[e]indole-2-carbonyl)-phenyl]-methanesulfonamide;
(5-Amino-3H-pyrrolo[3,2-f]isoquinolin-2-yl)-(3-methoxy-pyridin-4-yl)-methanone; and
(4-Amino-2-methyl-phenyl)-(9-hydroxy-3H-pyrrolo[2,3-c]quinolin-2-yl)-methanone.

* * * * *